United States Patent [19]

Ranney

[11] Patent Number: 5,260,050

[45] Date of Patent: * Nov. 9, 1993

[54] METHODS AND COMPOSITIONS FOR MAGNETIC RESONANCE IMAGING COMPRISING SUPERPARAMAGNETIC FERROMAGNETICALLY COUPLED CHROMIUM COMPLEXES

[76] Inventor: David F. Ranney, 3539 Courtdale Dr., Dallas, Tex. 75234

[*] Notice: The portion of the term of this patent subsequent to May 25, 2010 has been disclaimed.

[21] Appl. No.: 463,692

[22] Filed: Jan. 11, 1990

Related U.S. Application Data

[63] Continuation-in-part of Ser. No. 252,565, Sep. 29, 1988, filed as PCT/US89/04295, Sep. 29, 1989, abandoned.

[51] Int. Cl.⁵ .............. G01N 24/08; C07F 19/00; C07H 23/00; A61K 33/24
[52] U.S. Cl. .................. 424/9; 424/2; 424/617; 436/173; 436/806; 128/653.4; 556/61; 536/102; 536/112; 536/122
[58] Field of Search ............ 424/9, 617, 646, 2; 436/173, 806; 128/653.4, 654; 556/61; 536/102, 112, 122

[56] References Cited

U.S. PATENT DOCUMENTS

| | | | |
|---|---|---|---|
| 4,423,158 | 12/1983 | Porath | 521/32 |
| 4,452,773 | 6/1984 | Molday | 424/1.1 |
| 4,474,866 | 10/1984 | Ziolo | 430/106.6 |
| 4,647,447 | 3/1987 | Gries et al. | 424/9 |
| 4,731,239 | 3/1988 | Gordon | 424/9 |
| 4,735,210 | 4/1988 | Goldenberg | 424/4 |
| 4,735,796 | 4/1988 | Gordon | 424/9 |
| 4,770,183 | 9/1988 | Groman | 128/654 |
| 4,827,945 | 5/1989 | Groman et al. | 128/653 R |
| 4,832,877 | 5/1989 | Bino | 260/414 |
| 4,849,210 | 7/1989 | Widder | 424/9 |
| 4,951,675 | 8/1990 | Groman et al. | 128/653 CA |
| 4,957,939 | 9/1990 | Gries et al. | 514/492 |
| 4,963,344 | 10/1990 | Gries et al. | 424/9 |
| 4,965,007 | 10/1990 | Yudelson | 252/62.53 |

FOREIGN PATENT DOCUMENTS

| | | |
|---|---|---|
| 0186947 | 7/1986 | European Pat. Off. |
| 0190464 | 8/1986 | European Pat. Off. |
| WO87/02893 | 5/1987 | PCT Int'l Appl. |
| WO87/05031 | 8/1987 | PCT Int'l Appl. |
| WO88/00060 | 1/1988 | PCT Int'l Appl. |
| WO88/07365 | 10/1988 | PCT Int'l Appl. |
| 2137612A | 10/1984 | United Kingdom |
| WO85/05554 | 12/1985 | World Int. Prop. O. |

OTHER PUBLICATIONS

Bruner, Henri Chem. Abstracts 100:210,064h (1984).
Eremenko, Il. Chem. Abstracts 112:139311b (1990).
Komura, Y. Chem. Abstracts, 101:31379p (1984).
Lauffer et al., "Preparation and Water Relaxation Properties of Proteins Labeled with Paramagnetic Metal Chelates," *Mag. Res. Imag.* (1985) 3:11–16.
Bino et al. "$[Cr_4S(O_2CCH_3)_8(H_2O)_4](BF_4)_2 \cdot H_2O$: Ferromagnetically Coupled $Cr_4S$ Cluster with Spin 6 Ground State", *Science,* (1988) 241:1479–81.
Gallo et al., *Pharmaceutical Research,* 5:300–304 (1988).
International Search Report for International Application No. PCT/US89/04295, Jan. 8, 1990.

*Primary Examiner*—Glennon H. Hollrah
*Assistant Examiner*—Gary E. Hollinden
*Attorney, Agent, or Firm*—Arnold, White Durkee

[57] ABSTRACT

Improved compositions and methods for selective access to tumor regions (or other regions of abnormal endothelial properties). This capability provides powerful contrast-enhancement agents for nuclear magnetic resonance imaging. A polyatomic complex which includes intramolecular ferromagnetic coupling between metal atoms is associated with a polymer or microsphere carrier matrix which will bind to endothelial determinants. A solution containing this carrier complex is injected into a human (or other) body to be imaged. The carrier complex will preferentially extravasate at locations where the blood vessel walls have increased porosity or microvascular surface changes, and especially at tumor sites. Thus, the changes in relaxation time induced by the presence of the carrier complex will provide a high-gain marker for magnetic resonance imaging.

Multiple superparamagnetic polyatomic complexes are described, including novel complexes which include acetate and glycinate bridging ligands with a polyatomic metal-atom-complex core.

29 Claims, 12 Drawing Sheets

METHODS AND COMPOSITIONS FOR MAGNETIC RESONANCE IMAGING COMPRISING SUPERPARAMAGNETIC FERROMAGNETICALLY COUPLED CHROMIUM COMPLEXES

CROSS-REFERENCE TO OTHER APPLICATIONS

The present application is a continuation-in-part of U.S. application Ser. No. 07/252,565, filed Sep. 29, 1988, now abandoned, and claims priority therefrom under 35 USC §120, and is also a continuation-in-part of international (PCT) application PCT/US 89/04295, filed Sep. 29, 1989, and claims priority therefrom under 35 USC §120.

BACKGROUND AND SUMMARY OF THE INVENTION

The present invention relates to nuclear magnetic resonance imaging methods.

Nuclear Magnetic Resonance Imaging Generally

Atoms which have a magnetic moment will have sharply defined frequencies of nuclear oscillation in a strong magnetic field. This phenomenon is known as "nuclear magnetic resonance," or NMR. The frequency of oscillation of each atomic nucleus will depend on its mass, its dipole moment, the chemical bonding of the atom, the atom's environment (which will be affected by electromagnetic coupling to other atoms in the vicinity), and the strength of the magnetic field seen by the atom. Thus, the frequency of oscillation will be characteristic, not only of the various atomic species, but also of their molecular environments. By resonantly exciting these oscillations, the atomic species and their environments can be determined with accuracy.

If a pulse of RF energy is applied at a resonance frequency of atoms of a particular species and environment (e.g. hydrogen atoms in a water environment), the atomic nuclei of this type and environment will be excited into nuclear oscillation, and will later make a transition back to a low state of excitation. This transition will often be accompanied by emission of a radio-frequency signal, at the excitation frequency or a known lower frequency. (This emission is known as a "spin echo.") The spatial distribution of these "echoes" will provide a map of the distribution of atoms of the predetermined type and environment. Moreover, the time delay before the spin echo emission occurs will also give important information about the environment of the atom. (This time delay is referred to as the relaxation time.) Relaxation time analysis is generally used to provide additional detail in NMR imaging for medical purposes.

In the last decade, this technique has been applied to perform medical imaging. Living bodies can be imaged without harm, using the known resonance characteristics of (usually) protons in an aqueous environment. A strong DC magnetic field $B_0$ is used, together with gradient fields which are controlled so that the net total magnetic field will reach a predetermined value only in desired locations. A series of RF pulses is applied, while the magnetic bias fields are varied (using field-gradient coils) and the "spin echos" are detected. Since the magnetic field contours, and the resonance characteristics of the protons, are accurately known, the position where the spin echos originate can be accurately determined. By repeated pulse and measurement operations, a map of the distribution of aqueous protons (and, in some cases, of lipid protons) can be obtained. This imaging technique is referred to as "magnetic resonance imaging," or "MRI."

Much recent work has developed refined techniques, based on the general technique just described. The NMR phenomenon can be used to form images based merely on intensity, or time-domain windowing can be used to distinguish among atoms with differing relaxation times. Another variation is to precisely distinguish the spectral characteristics which are determined by the atomic environment of the nucleus, and this technique is referred to as spectral-shift imaging.

Magnetic resonance intensity, relaxation and spectral-shift images have been shown in recent years to provide an important, safe mode of brain and body imaging at very high spatial resolution (typically less than $0.6 \times 0.6$ mm in-plane resolution $\times 2$ mm-thick slices) of internal structures, organs and pathologic foci in live animals and humans. MRI potentially allows much smaller structures and tumors to be detected and monitored therapeutically than is possible by computed axial tomography (CAT) or radionuclide imaging, which typically resolve tumor masses only at 1 to 2.5 $cm^3$.

Clinical MRI is a rapidly growing form of brain and body imaging. This has proven to be a very useful diagnostic technique, and its use is rapidly increasing. The use of this technique for body imaging is beginning to increase above 10% of total cases. This increase has been accelerated as a result of the availability, on many of the standard clinical instruments, of such improved techniques as: more rapid, T1-weighted, narrow-flip-angle pulse sequences; efficient data processing; and respiratory and cardiac gating devices. Rapid images of acceptable quality can be acquired using near-real-time acquisitions of 15 seconds (a single breathholding interval) to 2 minutes. Proton MRI detects chemical parameters in the immediate environment around mobile protons of body water (principally) and fat. Changes in these parameters are often more sensitive, and frequently occur earlier in the course of disease, than those detected by CAT (tissue densities) or radionuclide imaging (gamma isotopic emissions from radionuclides localized in diseased tissues at sufficient concentrations above blood background). (See Runge et al., 141 *Am. J. Radiol.* 1209 (1983)). Nevertheless, in the absence of contrast agents, it has been difficult for MRI to detect very small tumors, especially those less than 2 $mm^3$ in brain and less than 5 $mm^3$ in the body.

Body MR images are less well resolved than brain images, for several reasons. Body imaging involves larger RF coils, with resulting lower magnetic field homogeneity and decreased sensitivity (decreased signal-to-noise ratio). Body imaging also can be affected by body motion artifacts. (The time required to do NMR body imagining on human patients is typically in the range of 1.5 to 7 minutes, depending on the imaging sequence used.) Additionally, it has been demonstrated that it is difficult for MRI (unless augmented by non-electronic means) to: 1) distinguish between viable (perfused) and necrotic (unperfused) tumor; 2) recognize biologically relevant tumor subregions which must be monitored at the very small sizes (1 $mm^3$) and early intervals (20 to 30 hours) required to assess early treatment effects before tumor nodules regrow to X-raydetectable and radionuclide-detectable sizes. The newly expanded repertoire of RF pulse sequences cannot compensate entirely for body motion artifacts.

NMR Image Enhancement

It has long been suggested that strongly paramagnetic species could be used as image-enhancers for nuclear magnetic resonance (NMR) imaging of living organisms. For example, efforts have been made to transport gadolinium ions (as ion chelates) into imaging sites, since gadolinium ions are strongly paramagnetic. However, it has not heretofore been possible to achieve highly selective transport of appropriate gadolinium-bearing species to the desired imaging sites.

Image contrast enhancement with potent, nontoxic, tumor-selective MRI contrast agents can overcome many of these problems by enhancing critical tumor structures (including tumor margins) and thereby shortening image-acquisition times.

Paramagnetic contrast agents decrease the relaxation time (T1-time preferentially) of mobile, rf-pulsed protons. This increases the local image intensity of tissues, organs, tumor matrix or tumor cells in which the agent becomes localized. The result is that small tumors (and other pathologic foci) are imaged (or their spectra monitored) with improved selectivity, sensitivity and precision of marginal definition.

Seven factors make it highly desirable to develop nontoxic MRI image-enhancing agents analogous to those available for CAT.

1. They increase the specificity of MRI diagnosis.
2. Smaller lesions can be identified earlier.
3. Image-enhancing agents enhance tumor masses differently than surrounding edema fluid or abscesses. This allows the extent and invasion of tumors to be defined more precisely. Lesions with infiltrative-type growth (e.g., certain metastatic carcinomas and glioblastomas) will require contrast agents for demarcation between tumor and edema fluid (Felix et al., 2 *Proc. Soc. Mag. Res. Med.* 831 (1985)).
4. Image-enhancing agents improve the distinction between recurrent tumor and fibrous tissue resulting from surgery and radiation.
5. Image-enhancing agents can decrease the time required per scan and potentially decrease the number of scans required per procedure. This increases the volume of procedures and decreases their expense.
6. Body imaging has a significantly lower resolution (typically 0.5-1.0 cm) and sensitivity (decreased signal-to-noise ratio) than brain imaging (see Wesbey et al., 149 *Radiology* 175 (1983), which is hereby incorporated by reference)). These differences result from the greater inhomogeneity of the magnetic field; the larger radio frequency coil; unequal phase-pulsing of deep versus shallow nuclei; and motion artifacts produced by respiration, cardiac systole, gastrointestinal peristalsis, and voluntary muscle movement.
7. Advanced (polymeric and microsphere) forms of contrast agents (see below) appear to be required for the optimal acquisition and interpretation of blood-flow and tissue-perfusion images and related spectral (phase) information.

Toxicity of the image-enhancing substance is not only undesirable per se, but also will necessarily limit the maximum dose which can be used, and therefore will limit the degree of image-enhancement which can be achieved.

The discrete intensities of a two-dimensional, Fourier-transformed image are described by the following general equation (for spin-echo pulse sequences):

$$\text{Intensity} = N(H) \cdot f(v) \cdot \exp(-TE/T2) \cdot (1 - \exp(TE - TR/T1)).$$

where:

$N(H)$ = number of protons in the discrete tissue volume (spin density);

$f(v)$ = a function of proton velocity and the fraction of protons which are moving (e.g., due to following blood);

TE = time between the radio frequency (rf) pulse and the detection of signal (spin-echo);

TR = the interval between repetition of the RF pulse.

T1 = the time interval associated with the rate of proton energy transfer to the surrounding chemical environment (spin-lattice relaxation);

T2 = the time interval associated with the rate of proton energy level transfer (spin-spin relaxation).

The T1 and T2 times have reciprocal effects on image intensity. Intensity is increased by either shortening the T1 time or lengthening the T2 time. Tissue contrast occurs naturally and is related to variations in the chemical environments around water protons (major contributor) and lipid protons (usually minor). Chemical agents have been used to enhance this natural contrast. The one most widely tested clinically is the paramagnetic metal ion, gadolinium. (See Runge et al., 141 *Am. J. Radiol.* 1209 (1983) (which is hereby incorporated by reference) and Weinman et al., 142 *Am. J. Radiol.* 619 (1984), which is also hereby incorporated by reference). Although gadolinium shortens both the T1 and T2 times, at the lower doses used for clinical imaging, the T1 effect generally predominates and the image becomes brighter. Also, the RF pulse sequence can be programmed to accentuate T1 changes and diminish those due to T2 (Runge et al., 141 *Am. J. Radiol.* 1209 (1983)(which is hereby incorporated by reference)). Hence, "T1-weighted" enhancement can be achieved by selecting the most favorable Gd dose and RF pulse sequence.

The shortening of proton relaxation times by Gd is mediated by dipole-dipole interactions between its unpaired electrons and adjacent water protons. The effectiveness of Gd's magnetic dipole drops off very rapidly as a function of its distance from these protons (as the sixth power of the radius). (See Brown, 3 *Mag. Res. Imag.* 3 (1985)(which is hereby incorporated by reference)). Consequently, the only protons which are relaxed efficiently are those able to enter Gd's first or second coordination spheres during the interval between the RF pulse and signal detection. This ranges from 105 to 106 protons sec$^{-1}$. (See Brown, 3 *Mag. Res. Imag.* 3.) Still, because Gd has the largest number of unpaired electrons (seven) in its 4f orbital, it has the largest paramagnetic dipole (7.9 Bohr magnetons) and exhibits the greatest paramagnetic relaxivity of any single element (Runge et al., 141 *Am. J. Radiol.* 1209 (1983), and Weinman et al., 142 *Am. J. Radiol.* 619 (1984)). Hence, Gd has the highest potential of any element for enhancing images. However, the free form of Gd is quite toxic. This results in part from precipitation at body pH (as the hydroxide). In order to increase solubility and decrease toxicity, Gd has been chemically chelated by small organic molecules.

In mid-1988, a first-generation, low-molecular-weight, paramagnetic contrast agent, gadolinium-diethylenetriaminepentaacetate (Gd-DTPA) dimeglumine, was approved for general clinical use (Berlex-Schering AG; West Germany patent filed by Gries, Rosenberg and Weinman: DE-OS 3129906 A 1 (1981)). This agent has significantly improved the assessment of brain and renal tumors. Nevertheless, its small molecular size causes it to: 1) diffuse freely into normal tissues as well as pathologic foci, thereby decreasing the magnitude and gradient of image contrast at tumor margins; and 2) backdiffuse rapidly from the tumor matrix into blood capillaries, resulting in a very short postinjection contrast interval of 10–45 minutes. This latter characteristic precludes the premedication of patients outside the imaging room. The presence of an intact blood-brain barrier in the normal tissue surrounding brain tumors, reduces the problem of normal brain enhancement by Gd-DTPA.

Despite its satisfactory relaxivity and toxicity, this formulation has four major disadvantages.

(1) Chelation of Gd markedly decreases its relaxivity (by half an order of magnitude). This happens because chelators occupy almost all of Gd's inner coordination sites, which coincide with the strongest portion of the paramagnetic dipole. (See Koenig, 2 *Proc. Soc. Mag. Res. Med.* 833 (1985)(which is hereby incorporated by reference), and Geraldes et al., 2 *Proc. Soc. Mag. Res. Med.* 860 (1985)(which is hereby incorporated by reference)).

(2) Gd-DTPA dimeglumine, like all small paramagnetic metal chelates, suffers a moderate decrease in relaxivity at the higher radio frequencies used clinically for proton imaging (typically 15 MHz). (See Geraldes et. al., 2 *Proc. Soc. Mag. Res. Med.* 860.)

(3) Due to its low molecular weight, Gd-DTPA dimeglumine is cleared very rapidly from the bloodstream (½ in 20 minutes), and also from tissue lesions (tumors). (See Weinman et al., 142 *Am. J. Radiol.* 619 (1984)). This limits the imaging window (to ca. 10 to 45 minutes); limits the number of optimal images after each injection (to ca. 2); and increases the agent's required dose and relative toxicity.

(4) The biodistribution of Gd-DTPA is suboptimal for imaging of body (versus brain) tumors and infections. This is due to its small molecular size. Intravenously administered Gd-DTPA exchanges rapidly into the extracellular water of normal tissues, as well as concentrates in tumors and infections. This is facilitated by the absence, in body organs, of the "blood-brain" vascular barrier which partly restricts the exchange of Gd-DTPA into the extracellular water of normal (versus diseased) brain. The result, in body organs, is a reduced difference in the concentration of Gd-DTPA between normal and diseased regions of tissue, and hence, reduced image contrast between the normal and diseased regions of the organ. Also, a disproportionate quantity (>90%) of Gd-DTPA is sequestered very rapidly in the kidneys. (See Weinman et al., 142 *Am. J. Radiol.* 619 (1984)). Of much greater interest to body MRI, are the abdominal and musculoskeletal-soft tissue sites involved in the early detection and staging of tumors (particularly body tumors, including the liver, spleen, bone marrow, colon, pancreas, and limbs).

Attempts have been reported to conjugate paramagnetic (principally gadolinium) chelates to protein carriers (principally albumin), by adding reactive chelate precursor molecules (principally DTPA anhydride) with the externally exposed amino groups of the intended carrier protein. However, due to the limited number of such amino groups on naturally occurring proteins, and the difficulty of forming amine conjugates, these protein carriers have suffered from low derivitization (substitution) ratios.

Comparably low substitution ratios (normalized for molecular weight) have been reported for immunoglobulins. (See Lauffer et al., 3 *Mag. Res. Imaging* 11 (1985)(which is hereby incorporated by reference), and Brady et al., 1983 Soc. Mag. Res. 2nd Ann. Mtg., *Works in Progress*, San Francisco, Calif.). Comparably low substitution ratios have also been reported for fibrinogen. (See Layne et al. 23 *J. Nucl. Med.* 627 (1982)(which is hereby incorporated by reference)). This results from the relative difficulty of forming amide bonds, the comparatively low number of exposed amino groups on typical proteins which are available for coupling, and the relatively rapid hydrolysis of DTPA anhydride coupling substrate which occurs in the aqueous solvents required to minimize protein denaturation during conjugation. (See Hnatowich et al., 33 *Int. J. Appl. Rad. Isot.* 327 (1982)(which is hereby incorporated by reference), and Krejcarek et al., 77 *Biochem. Biophys. Res. Comm.* 581 (1977)(which is hereby incorporated by reference)). The overall effect of these suboptimal conditions is that a very large dose of carrier material is required to achieve significant in vivo effects on MR images. At this high dose, the carrier produces an unacceptable acute expansion of the recipient's blood volume by an osmotic mechanism. Indeed, low substitution ratios have generally limited the use of such protein-chelator-metal complexes to the more sensitive (low-dose), radiopharmaceutical applications. (See Layne et al., 23 *J. Nucl. Med.* 627 (1982)(which is hereby incorporated by reference)).

An attempt to overcome this low substitution ratio has been made by conjugating DTPA to the non-protein carrier, cellulose (which is water insoluble). (See Bulman et al., 40 *Health Physics* 228 (1981)(which is hereby incorporated by reference).) However, the chemical method employed results in continued suboptimal substitution of DTPA to carrier. The nonbiodegradability of cellulose (which is water insoluble) and its water-soluble derivatives, and the reported molecular aggregation which results from organic-solvent conjugation (in dimethylformamide) of CNBr-activated cellulose to the diaminohexyl spacer groups which link the carrier to DTPA, have rendered this class of carrier-conjugates unacceptable for intravenous administration at the doses required for MR image enhancement.

A very important consideration in the image enhancement of solid tumors and inflammatory lesions by polymeric contrast agents is that, in order for these agents to extravasate (exit) efficiently from the microcirculation into adjacent diseased tissues, they must be completely soluble. For example, they must not be contaminated by intermolecular or supramolecular microaggregates. Optimal tumor access and localization requires that the molecular size of such agents generally be less than approximately 2,000,000 Daltons (ca. 2 to 3 nanometers in molecular diameter), and preferably less than 500,000 Daltons (ca. 0.5 to 1 nanometer in molecular diameter; see Jain, 1 *Biotechnology Progress* 81 (1985), which is hereby incorporated by reference), and most preferably, as taught by the present application, less than about 40,000 to 45,000 Daltons. For this reason, with rare exceptions (see Example 6, below), the particulate and microaggregate classes of contrast agents (which comprise the liposomes, colloids, emulsions, particles, microspheres and the larger microaggregates, as described below) do not concentrate efficiently in most solid tumors and inflammatory lesions.

Instead, following intravenous administration, these supramolecular-sized agents:

a) are first circulated in the bloodstream for relatively short intervals (2 minutes to 24 hours, depending on size), potentially allowing direct image enhancement of the blood pool (plasma compartment); and b) are subsequently cleared by specialized (phagocytic) cells of the reticuloendothelial tissues (liver, spleen and bone marrow), potentially allowing selective enhancement of these normal tissues, but producing indirect (negative) enhancement of lesions within these tissues (due to exclusion of the agents from the diseased regions).

Additionally, following installation into the gastrointestinal tract and other body cavities, these particulate and microaggregate classes of agents can produce direct image enhancement of the fluids within these cavities, and thereby potentially delineate mass lesions which encroach upon the lumens and cavities.

Both microspheres and microaggregates are supramolecular in size. The microaggregate class of agents is produced (intentionally or unintentionally) by either a) molecular cross-linking of individual polymer molecules or b) secondary aggregation of previously single (soluble) polymers, as induced by charge attraction or hydrophobic bonding mechanisms. It is distinguished from the microsphere class of agents by virtue of its smaller particle size, which ranges from approximately 2,000,000 Daltons (ca. 2 to 3 nanometers in diameter) to 0.1 micrometers (=100 nanometers in diameter). It is important to note that microaggregates are cleared by reticuloendothelial phagocytes with significantly less efficiency and rapidity than are microspheres. In general, this property makes microaggregates a less preferred class of agents for visualizing the liver, spleen and bone marrow under the usual conditions of clinical imaging, for which prompt post-injection contrast enhancement is required.

Gd-DTPA has been entrapped in liposomes in order to selectively enhance images of the reticuloendothelial organs (liver, spleen and bone marrow) and potentially the lungs. (Buonocore et al., 2 *Proc. Soc. Mag. Res. Med.* 838 (1985)(which is hereby incorporated by reference).) Liver clearance is mediated by phagocytic (Kupffer) cells which spontaneously remove these small (0.05 to 0.1 micron) particles from the bloodstream (Buonocore et al. (1985) 2 *Proc. Soc. Mag. Res. Med.* 838). (Particles larger than 3 to 5 micron are selectively localized in the lungs, due to embolic entrapment in lung capillaries.) A recent report indicates that the small-sized Gd-liposomes produce effective decreases in liver T1's (as determined spectroscopically without imaging): see Buonocore et al. (1985) 2 *Proc. Soc. Mag. Res. Med.* 838). Also, insoluble Gd-DTPA colloids have recently been reported to enhance MR images of rabbit livers under in vivo conditions (Wolf et al. (1984) 4 *Radiographics* 66 (which is hereby incorporated by reference)). However, three major problems appear to limit the diagnostic utility of these devices. The multilamellar, lipid envelopes of liposomes appear to impede the free diffusion of water protons into the central, hydrophobic cores of these carriers, as assessed by the higher doses of Gd required for in vitro relaxivities equivalent to Gd-DTPA dimeglumine (Buonocore et al. (1985) 2 *Proc. Soc. Mag. Res. Med.* 838). This increases the relative toxicity of each Gd atom.

Even more importantly, these same lipid components cause the carriers to interact with cell membranes of the target organs in a way which leads to a marked prolongation of tissue retention, with clearance times of up to several months. (See Graybill et al., 145 *J. Infect. Dis.* 748 (1982)(which is hereby incorporated by reference), and Taylor et al., 125 *Am. Rev. Resp. Dis.* 610 (1982)(which is hereby incorporated by reference).) Two adverse consequences result. First, image enhancement does not return to baseline in a timely fashion. This precludes re-imaging at the short intervals (ca. 1 to 3-weeks) needed to assess acute disease progression and treatment effects. Second, significant quantities of the liposomally entrapped Gd-DTPA may be transferred directly into the membranes of host cells. (See Blank et al. 39 *Health Physics* 913 (1980)(which is hereby incorporated by reference); Chan et al., 2 *Proc. Soc. Mag. Res. Med.* 846 (1985)(which is hereby incorporated by reference).) This can markedly increase the cellular retention and toxicity of such liposomal agents.

The consequences for Gd toxicity have not yet been reported. Protein (albumin) microspheres with entrapped Gd and Gd chelates have been prepared, and have been determined (by the present inventor and others: see Saini et al. (1985) 2 *Proc. Soc. Mag. Res. Med.* 896) to have only modest effects on T1 relaxivity in vitro. This is because most of the Gd as well as other entrapment materials are initially sequestered in the interior of these spheres, and are released very slowly as the spheres become hydrated (with $t_{\frac{1}{2}}$s of hours). (See Widder et al., 40 *Cancer Res.* 3512 (1980)(which is hereby incorporated by reference).) This phenomenon has been found by the present inventor to markedly reduce the acute (30-to-90-minute) relaxivity of each Gd atom to approximately 1/10th that of Gd-DTPA dimeglumine. Hence, both the quantity of carrier material and the toxicity of Gd are both unnecessarily high.

Emulsions of insoluble, gadolinium oxide particles have been injected into experimental animals, with significant image-enhancing effects on the liver. (Burnett et al. (1985) 3 *Magnetic Res. Imaging* 65). However, these particles are considerably more toxic than any of the preceding materials, and are inappropriate for human use.

Novel Compositions and Methods for Imaging

Because of the significant disadvantages of existing MR image contrast agents, the present inventor has formulated improved, second-generation prototype agents with reduced toxicity, increased selectivity of tumor and organ uptake, as well as a significant potential for enhancing blood flow images.

A very important consideration, as taught by the present application, is that the marker substance should preferably be selectively deposited at the tissue location which is sought to be imaged. Moreover, the present application also contains significant teachings, regarding how closely the paramagnetic marker substance is bound to the polymer, which are believed to provide substantial advantages over previous teachings. The present application provides a novel method for NMR imaging, wherein image contrast is very strongly enhanced by a selective transport method which introduces superparamagnetic material selectively into the desired imaging locations, and specifically into tumor locations. The present application also provides novel compositions of matter which are useful in implementing these methods.

MRI contrast enhancement can be improved moderately in the brain (and greatly in the body, which lacks the brain's tight blood-tissue barrier), by increasing the tumor selectivity of agent uptake.

Injected gadolinium exchanges off of its DTPA chelator at a slow but significant rate in vivo. The resulting free gadolinium forms insoluble oxides, clears slowly from the body, and may produce significant side effects. The present application permits major advantages to be gained, by substituting a less toxic, efficiently cleared, highly paramagnetic ion or polyatomic metalatom complex in an improved delivery process.

Chromium, in the form of $^{51}CrO_4{}^{-2}$, has been used extensively as a clinical agent for radionuclide labeling of platelets and red blood cells. Hexavalent chromate is converted within the red cell to the $Cr^{+3}$ cation, which binds tightly but not irreversibly to hemoglobin. $^{51}$Chromium elutes from red cells at an average rate of 0.93% per day. It is not reutilized by the body, but is cleared efficiently by excretory pathways. It is also of low toxicity in humans, even at relatively large doses. According to studies, in which neutrophils, tumor-cells and other biological targets have been labeled in vitro, $^{51}CrO_4$ has been shown to bind to several cytoskeletal and cytoplasmic proteins (actomyosin as well as hemoglobin), and also to adenine nucleotides. It has also been shown to be nontoxic in vitro at relatively high concentration, as assessed by sensitive measures of cellular metabolism, DNA synthesis and cell division.

When tested as a potential MRI contrast agent, chromium (+3) has only moderate potency compared to gadolinium (+3), which has the highest number of unpaired electrons (7) of any metal ion. On this basis, the low-molecular-weight gadolinium chelate, Gd-DTPA, was developed as the first clinical MRI contrast agent, even though its small retained fraction (usually less than 0.5%) is substantially more toxic than equivalent quantities of retained chromium, and chromium is cleared much more completely than is gadolinium.

Superparamagnetic Compounds

One class of highly paramagnetic compounds is those in which each molecule includes multiple highly magnetic ions with parallel spin vectors. While such intramolecular paramagnetic coupling does not imply that macroscopic ferromagnetic behavior will occur, it does imply that the resulting compound will be very strongly paramagnetic. Thus, such compounds are referred to as "superparamagnetic."

A recent article by Bino et al., "$[Cr_4S(O_2CCH_3)_8(H_2O)_4]$: Ferromagnetically Coupled $Cr_4S$ Cluster with Spin 6 Ground State", in the Sep. 16, 1988 issue of Science at page 1479, reported that the paramagnetic potency of chromium can be increased markedly by reformulating it as an intramolecularly ferromagnetically coupled cluster of four coordinated chromium ions, $Cr_4S(O_2CCH_3)_8(H_2O)_4{}^{+2}$. This new, divalent chromium-organic complex cation has 12 unpaired electrons (1.7 times as many as gadolinium), and a magnetic spin of $S=6$ (ground state). The effective magnetic moment of each $Cr^{+3}$ atom in the molecule is increased, due to stabilization of a coordination state which minimizes intramolecular antiferromagnetism.

The Bino et al. article refers to using the disclosed cation as a "spin label". (Spin labeling studies are normally in vitro studies.) The Bino et al. article also notes that the water ligands on the cation are potentially labile, so that the hydration sites would provide ligand bonding sites.

This tetra-chromium-sulfur-acetate complex is very advantageous for use in formulating MRI contrast agents of high potency and low toxicity. However, its small molecular size would cause it to equilibrate freely with the total extravascular (plasma+extracellular) water (as does Gd-DTPA), thereby reducing its potency and tumor selectivity.

Transport Properties of Polymeric Carrier

The present application teaches that major advantages can be gained by complexing or conjugating a superparamagnetic complex, such as $Cr_4S(O_2CCH_3)_8(H_2O)_4{}^{+2}$, to polymeric or microspheric carriers which restrict its biodistribution, increase its selectivity of tumor localization, and amplify its proton relaxivity by slowing its rotational correlation time.

The present inventor has disclosed, in earlier filings, a method for increasing both the chemical potency (proton relaxivity) and tumor selectivity of paramagnetic contrast agents (including Gd-DTPA), by conjugating them to water-soluble, biocompatible carbohydrate polymers (including dextrans), whose molecular size distribution ranges from just above the cutoff for filtration out of normal microvessels (ca. 15,000 Daltons) to just below the cutoff for rapid renal clearance (ca. 45,000 Daltons).

Optimal Size Range

Selectivity of tumor uptake is conferred by the polymeric size, in conjunction with characteristic changes in microvascular surface properties and an increase in porosity of malignant tumor microvessels. This allows the polymeric species (between 15,000 and 45,000 Daltons) to filter or become transported more efficiently out of microvessels into the extravascular compartment (tumor interstitium). Due to the low porosity of normal microvessels, polymeric contrast agents are not allowed to filter into the surrounding normal tissues. This property of selective partitioning by molecular size: 1) advantageously results in steeper contrast gradients and increased intensity differences between tumor and normal tissues, and 2) advantageously produces highly discrete identification of tumor margins.

Endothelial Binding

Tumor localization is also facilitated by the endothelial binding properties of polycarboxylated and polysulfated polyglucoses and polyols, including polyglycerols. (Simple polysaccharides will normally not adhere to the endothelial wall, unless the polysaccharide includes a charged surface group, such as sulfate, carboxyl, or dicarboxyl.)

It is newly recognized in this filing that such endothelial binding is reversible and, moreover, that release of such bound materials occurs much more slowly from tumor microvascular endothelium than from the endothelium of normal tissues. Such prolonged binding at pathologic foci results in selectively accentuated uptake into the tumor interstitial gel proximal to sites of vascular endothelial binding.

Transendothelial Migration

Active endothelial transport has been demonstrated for small molecules (e.g., glucose and insulin). However, no studies other those that of the present applicant are known to have shown such transport for larger molecules, or for molecules carried in a cargo format. It is now known (from the present applicant's histologic studies) that transendothelial migration of particles and molecular aggregates (larger than ca. 2 nm in diameter) can be accelerated by the application of appropriate surface coatings, preferably glycosaminoglycans or anionic polyglucoses or polyglycerols. (The glycosaminoglycans preferably include heparin, heparin derivatives and heparin fragments, but may also include dermatan sulfate, chondroitin sulfate, and other nature or modified glycosaminoglycans, including semisynthetic carboxylated glycosaminoglycans.) These surface coatings will bind multiply to receptors or antigens, which are either synthesized by endothelium or, although synthesized at other sites, become tightly associated with the endothelial surface. (See Ranney, 35 *Biochem. Pharmacology* 1063 (1986), which is hereby incorporated by reference). Such multiple binding typically involves complementary molecular interactions at more than 5 binding sites per molecule, and preferably more than 10 sites per molecule, and is termed adhesion, surface adhesion, or bioadhesion.

Following extravasation, these polymeric agents percolate through the tumor interstitial gel at a rate about 3 to 8 times slower than do small molecules, including Gd-DTPA. This causes the polymeric agents to be retained for prolonged intervals in the tumor interstitium (greater than 2.5 hours, as compared to about 10–45 minutes for Gd-DTPA), and to remain ("stay put") preferentially in the viable (versus necrotic) subregions. These two properties: 1) allow the agent to be injected at earlier times before imaging (and hence allowing premedication outside the imaging room); 2) permit tumor-treatment effects to be monitored in responding tumor subregions at early post-treatment intervals (at about 6–30 hours); and 3) allow viable and nonviable tumor to be distinguished at submillimeter resolution. This is because dead subregions cease to perfuse (and hence cease to take in the image-enhancing agents), while viable subregions continue to perfuse and take up image-enhancing agent. Partially damaged subregions continue to perfuse, and, since their microvessels typically have a still-further increased porosity (due to treatment-induced primary or secondary vascular damage), they allow the larger species of polydisperse polymer (as well as the smaller ones) to extravasate into the tumor gel. Hence, the partially damaged and potentially recoverable subregions achieve the brightest image intensity, because they accumulate the greatest quantity of polymeric contrast-enhancing agent.

A further new teaching of the present application is that these anionic glycosaminoglycans, polyglucoses and polyglycerols (and analogous compounds) undergo accentuated uptake by tumor cells, compared to the rate of uptake by normal cells in the same tissue region. This is based on the anionic (negatively charged) nature of side groups present on the polyglucose carriers, which engage the cellular uptake receptors of the anionic transport channels (pores) which are typically induced in hepatocellular carcinomas (hepatomas). Such anionic transport channels have also been found in several other tumor types tested to date (by the present applicant and others). These same transport channels are relatively uninduced in the normal cell counterparts. This property of anionic small molecules and macromolecules facilitates active tumor-cell accumulation of the carrier polymer (and its bound ligands) in vivo. This property is exploited, in the innovative method disclosed herein, to allow for prolonged tumor retention and imaging.

The following list sets out some of the major advantages of polymeric MRI contrast agents, as exemplified by Gd-DTPA-dextran (40,000, 60,000, or 70,000 Dalton carrier size):

1. Increased proton relaxivity, due to the slower rotational correlation time of polymeric versus small molecular formulation (about 4 to 7 times more T1 relaxivity than that of Gd-DTPA dimeglumine).
2. Restricted biodistribution in vivo (in about 10% versus 35% of body water—due to improved retention of polymers versus small molecules in the plasma compartment of normal tissues). This advantage in turn results in:
   a. a decreased dose of paramagnetic metal, and
   b. decreased toxicity (due to decreased normal tissue uptake).
3. Improved body and brain imaging, due to improved selectivity of tumor uptake. This helps to allow detection and monitoring of very small tumors (1–2 $mm^3$).
4. Improved image contrast gradient and magnitude at tumor margins. This too helps to allow detection and monitoring of very small tumors (1–2 $mm^3$).
5. Prolonged tumor imaging enhancement (greater than $2\frac{1}{2}$ hours, versus 10–45 minutes for Gd-DTPA dimeglumine). This prolonged enhancement of the tumor image allows:
   a. patient premedication outside the imaging room (which helps to maximize utilization of the very expensive imaging equipment); and
   b. acquisition of multiple sequential optimally contrast-enhanced images with different pulse parameters, and
   c. imaging of multiple body regions after a single dose of agent.
6. Complete solubility. This provides the advantages of:
   a. allowing rapid renal clearance (if less than 45,000 Daltons), and
   b. avoiding acute uptake by normal liver (unlike Gd-DTPA, which undergoes acute hepatic uptake at about 5–45 minutes, thereby obscuring the visualization of liver tumors during optimal imaging intervals, especially when using T1-weighted pulse sequences).
7. Lower osmolality at typical injection concentrations (e.g. about 285–330 mOsmols per kg of water, at an injection concentration of 100 mg/ml).
8. Acute (20 to 30-hour post-treatment) monitoring of tumor responses can be performed in vivo at submillimeter resolution. This is not possible with low molecular weight agents such as Gd-DTPA, because of their very rapid percolation through the tumor gel, which obscures the functionally important living and dead regions.
9. Rapid conjugation, of multiple (e.g. 25 to 100) paramagnetic ions per protein molecule, can occur, to antibodies and to other proteins and peptides. (Some example include: lymphokines (including interleukin 2); cytokines (including tumor necrosis factor and interferons); and other biopharmaceutical agents.) This conjugation occurs by linking the entire polymeric MRI contrast-enhancing agent to the antibody, protein, or peptide, using simple chemical reactions, such as Schiff-base and water-soluble carbodiimide reactions. This provides sufficient amplification (due to the paramagnetic or superparamagnetic signal effect) for the (polypeptide) protein molecule to be detected by MRI contrast enhancement, even at the very low tissue concentrations of protein which are typically achieved in tumor interstitium (about 1 to 2 micromolar).

It has previously been shown, by the present inventor as disclosed in a previous filing (International Application PCT/US88/01096), that IMFERON TM (which is a tightly bound, iron oxide-dextran complex of about 110,000 Daltons) achieves increased intramolecular paramagnetism (becomes superparamagetic), in a fashion similar to that of $Cr_4S(O_2CCH_3)_8(H_2O)_4{}^{+2}$. This complex is injected into patients for the purpose of achieving controlled iron release, over intervals of days to weeks, in order to treat iron deficiency anemia. Although it has been injected intravenously into patients, this must be done by controlled rather than bolus infusion, due to the release of a small fraction of its ionic iron which has been associated with acute toxicities. Hence, IMFERON TM is usually administered intramuscularly. These problems, together with the requirements, in MR image enhancement, of rapid intravenous administration of relatively large doses of the contrast agent, have precluded the effective use of IMFERON TM as an intravascular superparamagnetic contrast agent. However, this experimental evidence provides further confirmation that, as described below, metal coordinates of high potency and lower toxicity can be reformulated as polymeric agents (with a conjugation chemistry which is somewhat analogous to that of IMFERON TM). Such metal-coordinate-polymer agents can be administered for purposes of tumor-selective MR image enhancement, or alternatively to provide localized hysteresis superheating.

The preferred embodiments preferably use a biodegradable, water-soluble polymer (synthetic or derived from natural sources) which has repeating hydrophilic monomeric units (preferably carbohydrate or sugar residues) with a high frequency of hydroxyl (and/or, in certain embodiments, amino or sulfate) side groups. This polymer also includes additional charged functional groups, (complexing, chelating, or coordinate-forming functional groups), which may include (but are not limited to): amine; quaternary ammonium or other reactive nitrogen group; hydroxyl; carbonyl; aldehyde; carboxy; polycarboxy; sulfhydryl; sulfate; sulfonium; phosphate; polyphosphate; phosphonium; or other homo- or hetero-anions. These charged (or chelating or coordinateforming) functional groups have a formation constant for divalent or trivalent metal cations (or for the organo-metallic complexes which contain these divalent or trivalent metal catios) of at least about 108 (and typically more) at physiological temperature and pH. The conjugation of chelating groups to the polymer (or to form the copolymer) is carried out under chemical conditions and in a solvent which yields a completely soluble (singlet) form of the carrier and avoids significant contamination by microaggregates. The molar ratio of chelating agent/monomeric unit is preferably between about 1/5 and about 1/25. The molar ratio of chelating agent/monomeric unit is preferably between about 1/5 and about 1/25. This image-enhancing agent is biodegradable to intermediary metabolites, rapidly excretable chelates, polymers, oligomers, monomers or combinations thereof, all of which have low toxicity and are cleared overwhelmingly by the renal route. The term "low toxicity" used herein means having little significant toxic effects at usable dosages of the image-enhancing agents.

Use of Microaggregate or Microparticulate Carrier

In one class of embodiments, the polymeric carrier is used in the form of microspheres. As discussed above, these microspheres have been found (when appropriately surfaced with sites complementary to endothelial determinants) to transport through the more porous parts of the endothelium walls with high preference. This is particularly advantageous in transporting a relatively high dose of the desired substance into the abnormal tissue cells.

Such a microsphere is most preferably between 0.2 and 250 micron in diameter. The matrix of the microsphere is preferably a carbohydrate, and may be a carbohydrate such as heparin which also has multivalent binding capabilities. Dextran can also be used, and can also be coated with a multivalent binding agent such as heparin. Such a microsphere carbohydrate matrix can optionally include, as a multivalent binding agent, an exposed or covert lectin (or peptide, polypeptide, or drug substance) which is capable of binding endothelial surface determinants, enzymes, epiendothelial or subendothelial substances. (Note that the microsphere matrix may be coated with such a binding substance.)

In such embodiments, the microspheres of the novel material disclosed herein will bind to endothelia (or to epithelia dn their closely associated extracellular structures), with preference (and longer residence times) in the vicinity of tumors (or other biological lesions if desired). This preferential binding leads to preferential induction, since a bound microsphere may be totally or partially enveloped in, for example, less than 10 to 15 minutes. The interaction of the preferred microspheres with endothelia may produce an induction of the endothelia to undergo transient separation or opening. The opening of the endothelia exposes underlying substances to which (ideally) binding may occur.

The present application provides improved methods and compositions of matter for the selective tumor localization of ferromagnetically coupled image-enhancing agents, contrast agents or spectral shift agents. This permits improved acquisition of tumor, tissue or organ images or spectra from live animals by nuclear magnetic resonance imaging or spectroscopy.

Additional Novel Compositions of Matter

It should be noted that the present application described not only a number of novel methods, but also a number of novel compositions of matter, as set forth in greater detail below.

One novel teaching of the invention involves use of (I) a ferromagnetically coupled, multiply paramagnetic ion cluster (hereafter also designated the "superparamagnetic complex") which is multiply associated, by complexation (including ion pairing) or covalent conjugation, with (II) a soluble, hydrophilic, biocompatible, excretable polymeric carrier, comprising repeating hydrophilic monomeric units, or with (III) monomeric or oligomeric subunits of the final polymer, which, when combined with the paramagnetic ion cluster, associates with this cluster to form an "in-chain" heteropolymer, and wherein the polymer or polymer subunits (either derived from natural sources or synthetic) have repeating monomeric units with a high frequency of hydroxyl, carbonyl, aldehyde, carboxyl, sulfate, sulfonate, sulfonium, phosphate, phosphonate, phosphonium, amine, amino, or quaternary ammonium groups, singly or in combination on the polymer, and the polymer has a molecular diameter of less than about 12 nanometers, and contains less than about 5% (w/w) cross-linked or microaggregated species, all of low toxicity. The latter groups are for the purposes of either noncovalently binding the superparamagnetic complex or binding to target (including tumor) microvascular endothelium, or binding to both of the preceding entities.

The polymeric agent may optionally be formulated using an excipient counterion to achieve charge balance. Such excipient agents may include, for example, organic amines, preferably including N-methylglucamine (meglumine).

The superparamagnetic complex of the primary preferred embodiments uses a central tetrahedrally coordinated sulfur atom, surrounded by four octahedrally coordinated Chromium atoms, which are stablilized by bridging ligands (which join pairs of Cr atoms). In the embodiment of Example 10, eight bridging ligands are used, and they are all acetate groups. However, in other embodiments, other bridging ligands, and/or a different number of bridging ligands, may be used.

Alternative Carrier Compositions

The polymers most preferably used are heparin (or heparan sulfate), DTPA-hydroxyethyl-starch (DTPA-HES), or DTPA-dextran. However, of course, a large variety of other carrier polymers could be used instead. Note that the preferred polymer molecules are hydrophilic, which is required to provide the necessary environment for reliable NMR results.

Some of the other preferred polymer species include other dextrans, dextran sulfate, dextran carboxylate, dermatan sulfate, chondroitin sulfate, pentosan polysulfate, hydroxyethyl starch, carboxylated hydroxyethyl starch or CARBETIMER TM, carboxylated hydroxyethyl starch, and carboxylated dextrans in which the carboxylating groups consist essentially of multiple closely spaced carboxylates which are thereby capable of undergoing chelation-type or coordination-type binding with divalent or trivalent metal ions, or with polyatomic organometallic complex structures which include these metal ions.

The locations of the charged groups in the polymer can be readily modified, by methods well known to those skilled in the art, e.g. by introducing succinylate or glutarylate groups to extend the charge ion groups out from the polymer based structure. Thus, where it is desired to increase the affinity of the polyatomic unit being transported for the polymeric carrier molecule, the conformation of the polymer can optionally be modified in this fashion to achieve a better fit.

Alternative Bridging Ligands in a Superparamagnetic Complex

The bridging ligands in the superparamagnetic complex need not be limited to acetate groups. A wide variety of organocarboxylates may be used. Some examples of alternative bridging ligands include: formate; formaldehyde; glutaraldehyde; glycinate; succinate; acetylacetonate; malonate; propionate; glutarate; hydroxamate; oxalate; 2-bromoacetate; 2-sulfoethanoate, thiolacetate; and thioglycolate.

Use of Reactive Bridging Ligands

The embodiment described below, which includes at least some glycinates as bridging ligands, has the advantage that the glycinates contain sites which can assist in binding. Thus, a further secondary teaching is that the bridging ligand should contain a charged and/or activatable site.

Alternative Paramagnetic Species

The paramagnetic ion which is used in the superparamagnetic complex is most preferably chromium, but may alternatively be one or more of the following species: iron, nickel, manganese, cobalt, vanadium, molybdenum, tungsten, copper, platinum (particularly $^{195}Pt$), erbium, gadolinium, europium, dysprosium and holmium.

Alternative Stabilizing Anions

The superparamagnetic complex $Cr_4S(O_2CCH_3)_8$ is preferably stabilized with water, so that the full formula of this complex cation is $Cr_4S(O_2CCH_3)_8(H_2O)_4^{+2}$. However, other stabilizing species can be used, such as sulfate, halide, nitrate, carboxylate, phosphates, or other stabilizing anions. (Note that some of these anions will be displaced when the complex binds to the endothelia or epithelia.)

Additional Novel Methods

The present application also sets forth a generally applicable method for selective transport of a desired small polyatomic structure into tumors, or other regions of enhanced vascular porosity. Note that these novel teachings can be applied not only to the method of magnetic resonance imaging described, but also to a tremendous variety of other diagnostic and therapeutic uses.

Improved Hyperthermia Methods

The present application also provides improved methods for the selective tumor or tumor-cell localization of hyperthermia agents. The present application also provides a method for inducing selective hyperthermia in tumors or tumor cells, with reduced damage to healthy tissue, by microwave hysteresis superheating of tumor-localized agents. In this class of embodiments, the fraction of hyperthermia agents which has not localized in abnormal tissue is not likely to induce other localized hyperthermia, since almost all of this remaining fraction will be on or very close to blood vessel walls, i.e. will be located in regions which are efficiently cooled.

For example, one disclosed embodiment uses the selective transport mechanism to provide selectively localized hysteresis heating. In this embodiment, polymer-encapsulated transportation of superparamagnetic substances is used to achieve selective deposition in tumorous tissue. The high density of paramagnetic material in the tumorous tissue results in a greatly enhanced cross section for absorbing RF energy. Therefore, when RF energy is applied to induce heating, the tumorous regions will be preferentially heated, as is desired. Thus, the cancerous cells can be harmed with minimal damage to healthy tissue.

Similarly, the novel selective transport method disclosed can also be used to transport substances which will intensify X-ray, radionuclide, or ultrasonic imaging.

Improved Therapeutic Methods

In a further alternative class of embodiments, the disclosed novel transport methods can be used to preferentially transport chemotherapeutic substances into a tumor, as described below.

Further Points of Novelty

Among the novel teachings set forth in the present application is a method for magnetic resonance imaging, comprising the steps of: a) identifying a living vertebrate animal to be imagined; b) introducing into the blood stream of said animal a tracer, comprising a hydrophilic polymeric molecule which has a molecular weight greater than about 15,000 Daltons, and a relatively small polyatomic structure which is superparamagnetic; c) applying to said animal a strong magnetic field which includes a gradient; d) and applying to at least a portion of said animal an electromagnetic perturbation field at a radio frequency generally corresponding to a resonant frequency of a predetermined species at a magnetic field strength which falls within the range of field strengths applied to said animal by said strong magnetic field, and measuring radio frequency response to define a spatial map of magnetic resonance characteristics within tissues of said animal.

Also among the novel teachings set forth in the present application is a method for magnetic resonance imaging, comprising the steps of: a) identifying a living vertebrate animal to be imagined; b) introducing into the blood stream of said animal a tracer, comprising a hydrophilic polymeric molecule which has a molecular weight greater than about 15,000 Daltons, and a relatively small polyatomic structure which is superparamagnetic; c) applying to said animal a strong magnetic field which includes a gradient; d) applying to at least a portion of said animal an electromagnetic perturbation field at a radio frequency generally corresponding to a resonant frequency of a predetermined species at a magnetic field strength which falls within the range of field strengths applied to said animal by said strong magnetic field, and measuring radio frequency response to define a spatial map of magnetic resonance characteristics within tissues of said animal; e) analyzing said spatial map to determine the extent of tumors or other regions of enhanced vascular porosity.

Also among the novel teachings set forth in the present application is a method for magnetic resonance imaging, comprising the steps of: a) identifying a living vertebrate animal to be imagined; b) introducing into the blood stream of said animal a tracer, comprising a hydrophilic polymeric molecule which has a molecular weight greater than about 15,000 Daltons, and a relatively small polyatomic structure which is superparamagnetic; c) applying to said animal a strong magnetic field which includes a gradient; d) and applying to at least a portion of said animal an electromagnetic perturbation field at a radio frequency generally corresponding to a resonant frequency of a predetermined species at a magnetic field strength which falls within the range of field strengths applied to said animal by said strong magnetic field, and measuring radio frequency response to define a spatial map of magnetic resonance characteristics within tissues of said animal.

Also among the novel teachings set forth in the present application is a method for magnetic resonance imaging, comprising the steps of: a) identifying a living vertebrate animal to be imagined; b) introducing into the blood stream of said animal a tracer, comprising a hydrophilic polymeric molecule which has a molecular weight greater than about 15,000 Daltons, and a relatively small polyatomic structure which is superparamagnetic; c) applying to said animal a strong magnetic field which includes a gradient; d) applying to at least a portion of said animal an electromagnetic perturbation field at a radio frequency generally corresponding to a resonant frequency of a predetermined species at a magnetic field strength which falls within the range of field strengths applied to said animal by said strong magnetic field, and measuring radio frequency response to define a spatial map of magnetic resonance characteristics within tissues of said animal; e) analyzing said spatial map to determine the extent of tumors or other regions of enhanced vascular porosity.

Also among the novel teachings set forth in the present application is a method for magnetic resonance imaging, comprising the steps of: a) identifying a living vertebrate animal to be imagined; b) introducing into the blood stream of said animal a tracer, comprising a relatively small polyatomic structure which has intramolecular ferromagnetic coupling between at least two metal atoms thereof, and is bound to a polymeric molecule having a molecular weight which is greater than about 15,000 Daltons; c) applying to said animal a strong magnetic field which includes a gradient; d) and applying to said animal an electromagnetic perturbation field at a radio frequency generally corresponding to a resonant frequency of a predetermined species at a magnetic field strength which falls within the range of field strengths applied to said animal by said strong magnetic field, and measuring radio frequency response to define a spatial map of magnetic resonance characteristics within tissues of said animal; e) and repeating said step d), without introducing any additional tracer, during a period which extends for at least 100 minutes after said step b).

Also among the novel teachings set forth in the present application is a method for magnetic resonance imaging, comprising the steps of: a) identifying a living vertebrate animal to be imagined; b) introducing into the blood stream of said animal a tracer comprising a superparamagnetic small polyatomic structure which is non-covalently bound by ion pairs to a polymeric molecule which has a molecular weight greater than about 15,000 Daltons and which includes a relatively high density of charged groups; c) applying to said animal a strong magnetic field which includes a gradient; d) and applying to said animal an electromagnetic perturbation field at a radio frequency generally corresponding to a resonant frequency of a predetermined species at a magnetic field strength which falls within the range of field strengths applied to said animal by said strong magnetic field, and measuring radio frequency response to define a spatial map of magnetic resonance characteristics within tissues of said animal.

Also among the novel teachings set forth in the present application is a method for magnetic resonance imaging, comprising the steps of: a) identifying a living vertebrate animal to be imagined; b) introducing into the blood stream of said animal a tracer comprising a superparamagnetic polyatomic structure which is at least partly covalently bound to a polymeric molecule which has a molecular weight greater than about 15,000 Daltons; c) applying to said animal a strong magnetic field which includes a gradient; d) and applying to said animal an electromagnetic perturbation field at a radio frequency generally corresponding to a resonant frequency of a predetermined species at a magnetic field strength which falls within the range of field strengths applied to said animal by said strong magnetic field, and measuring radio frequency response to define a spatial map of magnetic resonance characteristics within tissues of said animal.

Also among the novel teachings set forth in the present application is a method for magnetic resonance imaging, comprising the steps of: a) identifying a living vertebrate animal to be imagined; b) introducing into the blood stream of said animal a tracer, comprising microspheres of a hydrophilic polymeric molecule which has a molecular weight greater than about 15,000 Daltons, and a relatively small polyatomic structure which is superparamagnetic and which is bound to the interior of said polymeric molecule; c) applying to said animal a strong magnetic field which includes a gradient; d) and applying to at least a portion of said animal an electromagnetic perturbation field at a radio frequency generally corresponding to a resonant frequency of a predetermined species at a magnetic field strength which falls within the range of field strengths applied to said animal by said strong magnetic field, and measuring radio frequency response to define a spatial map of magnetic resonance characteristics within tissues of said animal.

Also among the novel teachings set forth in the present application is a method as above, wherein the polymeric molecule has a diameter of about 120 Ångstroms or less.

Also among the novel teachings set forth in the present application is a method as above, wherein said small polyatomic structure comprises plural paramagnetic atoms which are mutually ferromagnetically coupled.

Also among the novel teachings set forth in the present application is a method as above, wherein said small polyatomic structure is a complex ion.

Also among the novel teachings set forth in the present application is a method as above, wherein said small polyatomic structure consists essentially of $[Cr_4S(O_2CCH_3)_8(H_2O)_4]^{2+}$.

Also among the novel teachings set forth in the present application is a method as above, wherein said small polyatomic structure comprises multiple paramagnetic atoms selected from the group consisting of chromium, copper, nickel, manganese, erbium, gadolinium, erbium, dysprosium and holmium.

Also among the novel teachings set forth in the present application is a method as above, wherein said polymer is selected from the group consisting of: dextran, dextran sulfate, dextran carboxylate, heparin, heparan sulfate, dermatan sulfate, chondroitin sulfate, pontosan polysulfate, CARBETIMER TM, hydroxyethylstarch, and carboxylated hydroxyethylstarch.

Also among the novel teachings set forth in the present application is a method as above, wherein said polymeric molecule has a diameter of about 85 Ångstroms or less.

Also among the novel teachings set forth in the present application is a method as above, wherein said small polyatomic structure comprises multiple metal ions ferromagnetically linked together.

Also among the novel teachings set forth in the present application is a method as above, wherein said all constituents of said small polyatomic structure have very low toxicity, and said polyatomic structure is only loosely bound to said polymeric molecule.

Also among the novel teachings set forth in the present application is a method as above, wherein multiple ones of said polymeric molecule are physically combined in a microsphere having a diameter in the range of about 0.1 micron to 1 microns inclusive.

Also among the novel teachings set forth in the present application is a method as above, wherein said small polyatomic structure is a cation which comprises multiple metal ions ferromagnetically linked together.

Also among the novel teachings set forth in the present application is a method as above, wherein said small polyatomic structure is a cation which comprises multiple metal ions complexed with multiple organic groups.

Also among the novel teachings set forth in the present application is a method as above, wherein said small polyatomic structure is an ion which comprises metal ions, and wherein said metal ions have very low toxicity.

Also among the novel teachings set forth in the present application is a method as above, wherein said small polyatomic structure is ion-pair bound to the interior of said polymeric molecule.

Also among the novel teachings set forth in the present application is a method as above, wherein said small polyatomic structure is covalently bound to the interior of said polymeric molecule by bonds which include at least one metal-oxide bond.

Also among the novel teachings set forth in the present application is a method as above, wherein a substantial fraction of said charged groups on the interior of said polymeric molecule are selected from the group consisting of: sulfides, amides, sites whose charge is strongly affected by an ether bond, and halides.

Also among the novel teachings set forth in the present application is a method as above, wherein said polymeric molecule has a molecular weight which is less than about 45,000 Daltons.

Also among the novel teachings set forth in the present application is a method as above, wherein said polymeric molecule has a molecular weight which is less than about 70,000 Daltons.

Also among the novel teachings set forth in the present application is a method as above, wherein said polymeric molecule has anionic groups at the surface thereof.

Also among the novel teachings set forth in the present application is a method as above, wherein said perturbation field is applied at a frequency which generally corresponds to a resonance frequency of protons in an aqueous environment.

Also among the novel teachings set forth in the present application is an agent for image enhancement, spectral shift, or augmentation of hysteresis heating, comprising: a strongly paramagnetic or superparamagnetic polyatomic structure cation complex having a spin of greater than 3/2, more than about 7 unpaired electrons and labile or reactive ligands which can chemically or physically associate with: a biocompatible, excretable, water-soluble polymer comprising repeating hydrophilic monomeric units having hydroxyl, carboxylate, sulfate, phosphate, aldehyde or amine groups, singly or in combination on said polymer: wherein said image enhancing agent has a molecular diameter of less than about 12 nanometers and is substantially completely water-soluble.

Also among the novel teachings set forth in the present application is an agent for image enhancement, spectral shift, or augmentation of hysteresis heating, comprising: a ferromagnetically intramolecularly coupled paramagnetic cation complex having a spin of greater than 3/2, more than about 7 unpaired electrons and labile or reactive ligands which can chemically or physically associate with: a biocompatible, excretable, water-soluble polymer comprising repeating hydrophilic monomeric units having hydroxyl, carboxylate, sulfate, phosphate, aldehyde or amine groups, singly or in combination on said polymer: wherein the image enhancing agent has a molecular diameter of less than about 12 nanometers and contains less than about 5% (w/w) cross-linked or microaggregated species, all of low toxicity.

Also among the novel teachings set forth in the present application is an agent as above, comprising ferromagnetically clustered paramagnetic metal ions in association with the carrier, and wherein the image-enhancing agent is used to enhance internal images or shift internal spectra arising from induced magnetic resonance signals.

Also among the novel teachings set forth in the present application is an agent as above, wherein said polymer has a molecular weight between about 1,000 and 200,000 Daltons.

Also among the novel teachings set forth in the present application is an agent as above, wherein said polymer has a molecular weight between 20,000 and 70,000 Daltons.

Also among the novel teachings set forth in the present application is an agent as above, wherein said ferromagnetically coupled paramagnetic cation complexes are bound to said polymer noncovalently by a strong ionic (paired-ion or charge) interaction.

Also among the novel teachings set forth in the present application is an agent as above, wherein said polymer has a molecular weight between 20,000 and 70,000 Daltons, and said ferromagnetically coupled paramagnetic cation complex is bound to said polymer by carboxylate or sulfate groups which are covalently conjugated to said polymer.

Also among the novel teachings set forth in the present application is an agent as above, wherein said paramagnetic metal ions are selected from said group consisting of chromium, copper, nickel, manganese, erbium, gadolinium, erbium, dysprosium and holmium.

Also among the novel teachings set forth in the present application is an agent as above, wherein said ferromagnetically coupled paramagnetic cation complex is in a molar ratio of between about 1/5 and about 1/25 to the monomeric unit.

Also among the novel teachings set forth in the present application is an agent as above, wherein said polymer is selected from the group consisting of: dextran, dextran sulfate, dextran carboxylate, heparin, heparan sulfate, dermatan sulfate, chondroitin sulfate, pontosan polysulfate, CARBETIMER TM, hydroxyethylstarch, carboxylated hydroxyethylstarch.

Also among the novel teachings set forth in the present application is an agent as above, wherein said ferromagnetically coupled paramagnetic cation complex consists essentially of $[Cr_4S(O_2CCH_3)_8(H_2O)_4]^{2+}$, and said polymer consists essentially of DTPA-dextran.

Also among the novel teachings set forth in the present application is an agent as above, wherein said ferromagnetically coupled paramagnetic cation complex is $[Cr_4S(O_2CCH_3)_8(H_2O)_4]^{2+}$ and said polymer is heparin.

Also among the novel teachings set forth in the present application is an agent as above, wherein said ferromagnetically coupled paramagnetic cation complex is $[Cr_4S(O_2CCH_3)_8(H_2O)_4]^{2+}$ and said polymer is DTPA-hydroxyethylstarch.

Also among the novel teachings set forth in the present application is an agent as above, wherein said excess anionic charges of said polymer are balanced in part or totally by a nontoxic organic cation (base).

Also among the novel teachings set forth in the present application is an agent as above, wherein excess anionic charge of said polymer is balanced by N-methylglucamine (meglumine).

Also among the novel teachings set forth in the present application is an agent as above, wherein said ferromagnetically coupled paramagnetic cation complex is covalently conjugated to said polymer.

Also among the novel teachings set forth in the present application is an agent as above, wherein said ferromagnetically coupled cation complex is covalently conjugated to said polymer totally or in part by a metal oxide linkage.

Also among the novel teachings set forth in the present application is an agent as above, wherein said ferromagnetically coupled cation complex is covalently conjugated to said polymer totally or in part by a metal oxide linkage, and said ferromagnetically coupled cation complex is $[Cr_4S(O_2CCH_3)_8(H_2O)_4]$ and said polymer is dextran.

Also among the novel teachings set forth in the present application is an agent as above, wherein said ferromagnetically coupled cation complex is covalently conjugated to said polymer totally or in part by a metal oxide linkage, and said ferromagnetically coupled cation complex is $[Cr_4S(O_2CCH_3)_8(H_2O)_4]$ and said polymer is heparin.

Also among the novel teachings set forth in the present application is an agent as above, wherein said ferromagnetically coupled cation complex is covalently conjugated to said polymer totally or in part by a metal oxide linkage, and said ferromagnetically coupled cation complex is $[Cr_4S(O_2CCH_3)_8(H_2O)_4]$ and said polymer is hydroxyethylstarch.

Also among the novel teachings set forth in the present application is an agent as above, wherein said polymer with bound ferromagnetically coupled paramagnetic cation cluster has a microsphere physical form stabilized by heat or chemical treatment and with a diameter between about 0.1 micron and 250 micron.

Also among the novel teachings set forth in the present application is an agent as above, wherein said polymer with bound ferromagnetically coupled paramagnetic cation cluster has a microsphere physical form stabilized by heat or chemical treatment and with a diameter between about 0.1 micron and 250 micron, and said ferromagnetically coupled paramagnetic cation is $[Cr_4S(O_2CCH_3)_8(H_2O)_4]$ bound to DTPA-dextran and said microsphere diameter is between about 0.1 and about 1.0 micron.

Also among the novel teachings set forth in the present application is an agent as above, wherein said polymer with bound ferromagnetically coupled paramagnetic cation cluster has a microsphere physical form stabilized by heat or chemical treatment and with a diameter between about 0.1 micron and 250 micron, and said ferromagnetically coupled paramagnetic cation is $[Cr_4S(O_2CCH_3)_8(H_2O)_4]$ bound to DTPA-hydroxyethylstarch and said microsphere diameter is between about 0.1 and about 1.0 micron.

Also among the novel teachings set forth in the present application is an agent as above, wherein said polymer with bound ferromagnetically coupled paramagnetic cation cluster has a microsphere physical form stabilized by heat or chemical treatment and with a diameter between about 0.1 micron and 250 micron said ferromagnetically coupled paramagnetic cation is [$Cr_4S(O_2CCH_3)_8(H_2O)_4$] bound to DTPA-hydroxyethylstarch and said microsphere diameter is between about 0.1 and about 1.0 micron.

Also among the novel teachings set forth in the present application is an agent as above, wherein said ferromagnetically coupled paramagnetic cation is [$Cr_4S(O_2CCH_3)_8(H_2O)_4$] bound to Heparin and said microsphere diameter is between about 0.1 and about 1.0 micron.

Also among the novel teachings set forth in the present application is an agent as above, wherein said ferromagnetically coupled paramagnetic cation complex consists essentially of [$Cr_4S(O_2CCH_3)_8(H_2O)_4$]$^{2+}$, and said polymer consists essentially of DTPA-dextran, and said polymer is ion-pair bonded to said ferromagnetically coupled paramagnetic cation complex.

Also among the novel teachings set forth in the present application is an agent as above, wherein said ferromagnetically coupled paramagnetic cation complex is [$Cr_4S(O_2CCH_3)_8(H_2O)_4$]$^{2+}$ and said polymer is heparin, and said polymer is ion-pair bonded to said ferromagnetically coupled paramagnetic cation complex.

Also among the novel teachings set forth in the present application is an agent as above, wherein said ferromagnetically coupled paramagnetic cation complex is [$Cr_4S(O_2CCH_3)_8(H_2O)_4$]$^{2+}$ and said polymer is DTPA-hydroxyethylstarch, and said polymer is ion-pair bonded to said ferromagnetically coupled paramagnetic cation complex.

Also among the novel teachings set forth in the present application is an agent as above, wherein said ferromagnetically coupled paramagnetic cation complex is [$Cr_4S(O_2CCH_3)_8(H_2O)_4$]$^{2+}$ and said polymer is CARBETIMER ™, and said polymer is ion-pair bonded (via aldehyde or amine groups) to said ferromagnetically coupled paramagnetic cation complex.

Also among the novel teachings set forth in the present application is an agent as above, wherein said ferromagnetically coupled paramagnetic cation complex is [$Cr_4S(O_2CCH_3)_8(H_2O)_4$]$^{2+}$ and said polymer is pentosan polysulfate, and said polymer is ion-pair bonded (via sulfate groups) to said ferromagnetically coupled paramagnetic cation complex.

Also among the novel teachings set forth in the present application is a method for selective hysteresis heating, comprising the steps of: a) identifying a living vertebrate animal in which tumors are desired to be selectively heated; b) introducing into the blood stream of said animal an RF absorber, comprising a hydrophilic polymeric molecule which has a molecular weight greater than about 15,000 Daltons, and a relatively small polyatomic structure which is superparamagnetic; c) applying radio frequency energy to said animal at a relatively high field strength.

Also among the novel teachings set forth in the present application is a selective hysteresis heating method as above, wherein said radio frequency energy is applied at a frequency greater than 100 MHz.

Also among the novel teachings set forth in the present application is a selective hysteresis heating method as above, wherein said radio frequency energy is applied at a microwave frequency.

BRIEF DESCRIPTION OF THE DRAWING

The present invention will be described with reference to the accompanying drawings, which show important sample embodiments of the invention and which are incorporated in the specification hereof by reference, wherein:

FIG. 5A shows an infrared spectrum trace for the reaction products where $Cr_4S(O_2CCH_3)_8$ was heated with glycine in water at 92° C. FIG. 5B shows a trace for the reaction products where $Cr(NO_3)_3$ was heated with glycine in water at 92° C. FIG. 5C shows a trace for the reaction products where $Cr_4S(Ac)_8$ was refluxed in acetic anhydride for severals. FIG. 5D shows a trace for $Cr_4S(Ac)_8$ alone (which has a blue or green color), and FIG. 5E shows a trace for glycine alone.

DESCRIPTION OF THE PREFERRED EMBODIMENTS

The numerous innovative teachings of the present application will be described with particular reference to the presently preferred embodiment, wherein these innovative teachings are advantageously applied to the particular problems of NMR imaging by selective transport of superparamagnetic small molecules. However, it should be understood that this embodiment is only one example of the many advantageous uses of the innovative teachings herein. For example, the various types of innovative methods disclosed herein can optionally be used to transport acoustic image enhancers, or therapeutic substances. In general, statements made in the specification of the present application do not necessarily delimit any of the various claimed inventions. Moreover, some statements may apply to some inventive features but not to others.

Figure 2:
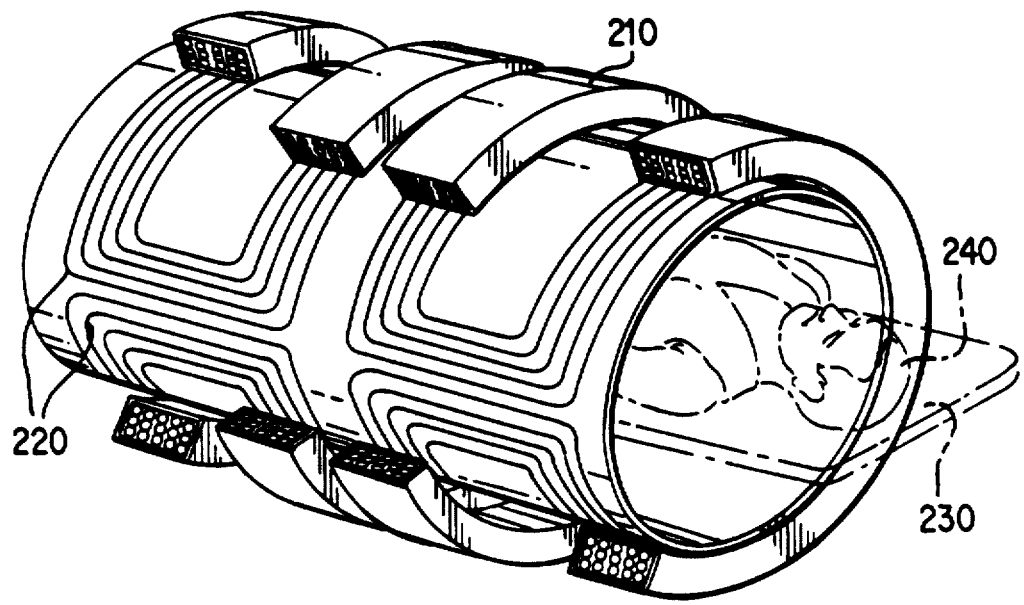
FIG. 2 schematically shows a nuclear magnetic resonance imaging system suitable for use in the disclosed innovative method.

FIG. 2 shows an example of a nuclear magnetic resonance imaging (MRI) unit, useable for whole-body imaging of human patients. A patient 240 is inserted, on a sliding table 230, into the interior of a large solenoidal winding 210. The large coils 210 (which may be watercooled or superconducting) will apply a constant (DC) magnetic field, typically 0.5 to 1 Tesla. (This field component is referred to as the $B_0$ field.) Bias coils 220 apply a gradient to this field, as described above. Finally, a probe coil (which is movable, and is not shown in this Figure) is used to apply the RF pulses described above. Differently shaped probe coils are used for imaging different parts of the body, and the probe coil is often shaped so that it will nearly fit to the shape of the surface of the area to be imaged.

The present invention provides an improved NMR imaging method, whereby the ability of NMR systems to detect tumors is greatly enhanced. This is accomplished by selectively introducing an image-enhancing, spectral shift responsive agent into the abnormal tissue.

One novel teaching of the invention involves use of (I) a ferromagnetically coupled, multiply paramagnetic ion cluster (hereafter also designated the "superparamagnetic complex") which is multiply associated by complexation (including ion pairing), coordination, or covalent conjugation; with (II) a soluble, hydrophilic, biocompatible, excretable polymeric carrier, comprising repeating hydrophilic monomeric units; or with (III) monomeric or oligomeric subunits of the final polymer, which when combined with the paramagnetic ion cluster, associates with this cluster to form an "in-chain" heteropolymer, and wherein the polymer or polymer subunits (either derived from natural sources or synthetic) have repeating monomeric units with a high frequency of hydroxyl, carboxyl, carbonyl, aldehyde, sulfate, sulfonate, sulfonium, phosphate, phosphonate, phosphonium, amine, amino, or quaternary ammonium groups, singly or in combination on the polymer; and the polymer has a molecular diameter of less than about 12 nanometers, and contains less than about 5% (w/w) cross-linked or microaggregated species, all of low toxicity. The latter groups are for the purposes of either noncovalently binding the superparamagnetic complex or binding to target (including tumor) microvascular endothelium, or binding to both of the preceding entities. The polymeric agent may be formulated using an excipient counterion to achieve charge balance, which may include organic amines, preferably including N-methylglucamine (meglumine). Preferred polymers include heparin, heparan sulfate, dextrans, dextran sulfate, dextran carboxylate, dermatan sulfate, chondroitin sulfate, pentosan polysulfate, hydroxyethyl starch, carboxylated hydroxyethyl starch or CARBETIMER TM, and especially heparin, carboxylated hydroxyethyl starch and carboxylated dextrans in which the carboxylating groups consist essentially of multiple closely spaced carboxylates which are thereby capable of undergoing chelation-type or coordination-type binding with divalent or trivalent metal ions, or with polyatomic organometallic complex structures which include these metal ions.

The ferromagnetically coupled paramagnetic complex includes a molecular coordination compound containing a paramagnetic metal ion present in numbers of two or more per molecular coordinate, wherein the paramagnetic metal ion includes one or more of the following: chromium, iron, nickel, manganese, cobalt, vanadium, molybdenum, tungsten, copper, platinum (particularly $^{195}$Pt), erbium, gadolinium, europium, dysprosium or holmium; and the coordinated metal ions are stabilized in a ferromagnetic or superparamagnetic intramolecular complex configuration by an external complexing substance. The preferred metal ions include chromium and gadolinium, and the preferred external complexing substances includes organosulfates and their derivatives, carboxylic acids, and especially acetate ions. The molecular coordinate may also include a central multivalent stabilizing ion or element, in which case the preferred element includes sulfur. The ferromagnetically coupled, paramagnetic complex (superparamagnetic complex) preferably has a net nuclear spin of greater than about 3/2 and has more than about 7 unpaired electrons. It has labile water groups and a net electrical charge, or reactive groups or combining sites which allow it to chemically associate, covalently or noncovalently with the carrier polymer.

In operation, time-domain windowing may be performed in the NMR imaging run, so that the atoms with the shortest relaxation times are seen preferentially. Alternatively, a high pulse repetition rate may be used, so that the tissues with the longest relaxation times are kept in saturation.

One preferred group of features of the complex for chemical association includes carboxylate, oxygen, metal (especially chromium "hydroxide") glycine amine, and net cationic (positive) charge.

One preferred embodiment involves providing the superparamagnetic coordinate $Cr_4S(O_2CCH_3)_8(H_2O)_4^{+2}$ as a noncovalent complex with heparin of about 22,000 Daltons, wherein the superparamagnetic coordinate binds via its cationic charges to the negatively charged sulfate groups of heparin at a molar ratio of about 1 superparamagnetic coordinate to every 2 to 25 monomeric units of the heparin and all or part (or none) of the excess free sulfate groups are balanced by ion pairing with N-methylglucamine. An alternative preferred embodiment includes an analogous formulation, wherein the superparamagnetic coordinate is complexed with low-molecular-weight hydroxyethyl starch (of less than about 50,000 Daltons) which also carries covalently bound diethylenetriamine pentaacetic acid (DTPA) side groups at a molar ratio of about 1 side group for every 5 to 25 monomeric units. Another alternative preferred embodiment includes an analogous formulation, wherein the superparamagnetic coordinate is complexed with dextran of 40,000 or 60,000 Daltons, which also carries covalently bound diethylenetriamine pentaacetic acid (DTPA) side groups at a molar ratio of about 1 side group for every 5 to 25 monomeric units. In alternative preferred embodiments of this class, the superparamagnetic complex binds to the sulfate groups of dextran sulfate or pentosan polysulfate.

The heparin superparamagnetic paired-ion complexes just described, are preferred for selective uptake by lung, lung tumors and other lung lesions, for MR image enhancement, or hysteresis hyperthermia, following intravenous injection, or for uptake by solid tumors and other focal disease following selective arterial administration. Lung uptake can be increased by leaving a sufficient fraction of heparin's sulfate groups, preferably greater than 30%, unbalanced by counterions. Lung uptake can be reduced and systemic access increased by balancing more completely the negative sulfate groups of heparin with either or both of the superparamagnetic complex or the excipient counterion, including N-methylglucamine.

The DTPA-dextran and DTPA-hydroxyethylstarch (DTPA-HES) complexes with the superparamagnetic substance just described are preferred for selective uptake, MR image enhancement, or hysteresis hyperthermia at systemically distributed sites of disease, including tumors, when administered by either intravenous or intraarterial injection. This is based on reduced lung clearance of the less acidic carboxylic acid (versus sulfate) side groups, which reduces binding to normal (versus lesional, including tumor) endothelium. It is also based on the lower degree of molecular complementarity of DTPA-dextran and DTPA-HES polymers with their endothelial binding substituents, which comprise heparan sulfates.

A second preferred embodiment involves providing the superparamagnetic coordinate, $Cr_4S(O_2CCH_3)_8(H_2O)_4^{+2}$, as a covalent complex with a biocompatible water-soluble excretable carbohydrate polymer, especially dextran of about 40,000 or 60,000 Daltons, or to hydroxyethyl starch of less than about 50,000 Daltons, wherein the superparamagnetic coordinate binds via a metal-oxide bond of chromium to the hydroxyl groups of dextran or hydroxyethyl starch at a molar ratio of about 1 superparamagnetic coordinate to every 2 to 25 monomeric units of the carbohydrate. An alternative preferred embodiment includes an analogous covalent conjugate of $Cr_4S(O_2CCH_3)_8(H_2O)_4^{+2}$ to carboxylated carbohydrate polymers, especially to DTPA-dextran of about 40,000 or 60,000 Daltons, or to DTPA-hydroxyethyl starch of less than about 50,000 Daltons, wherein the superparamagnetic coordinate binds via a metal-oxide bond of chromium to the carboxyl oxygen of the DTPA side groups on the polymer.

In certain instances, it may be preferable to separate the bound superparamagnetic substance from the polymeric carrier, using a linker which has a chain length of preferably between about 4 and 8 carbon atoms. This may be desirable under circumstances in which a) the superparamagnetic substance is a bulky molecule, or b) it is important to stabilize the bond between the polymer and the linker against lysis, including hydrolysis and esterolysis, which may in unusual cases, be catalyzed by a substituent of the superparamagnetic substance.

In an alternative embodiment, a method of modifying the spatial relation of the magnetic substance to carboxylated carbohydrate polymers, is specified. This alternative method involves derivatizing the carbohydrate polymer with a higher bifunctional acid, including preferably succinic acid, to form a succinylated polymer with a 4-carbon spacer between the polymer and the superparamagnetic to be conjugated to the polymer via the free carboxylate group of each succininate linker.

Although the preceding preferred methods of conjugation have focused on ester and carboxylate linkages, other linkers are not excluded, and in some cases may be preferred. These include aldehyde, amine, amide, carbodiimide, halogen-activated carbohydrate groups, and combinations thereof.

A third preferred embodiment involves providing a physical microsphere or nanosphere form of the preceding agents, in which the diameter of the spheres ranges from 0.1 to 250 micrometers, and the particles are preferably formed from their paired, polymer-superparamagnetic ion complexes or from simple mixtures of the polymer and the substance to be entrapped. Matrix polymers and excipients preferably comprise 50-75% of the particle weight. The particles are prepared preferably by phase emulsification (for larger ones) or high-pressure homogenization (for smaller ones), followed by heat or chemical stabilization of the polymer matrix, and extraction of the oil phase with an organic solvent, including acetone, ether, or hexane, preferably acetones which may also contain a small quantity of a biocompatible detergent for surface stabilization, preferably Tween 80 (or deoxycholate) at about 0.05 to 0.5% (w/w). Smaller particles are provided by high pressure homogenization. The degree of heat or chemical stabilization will preferably determine how long the particle retains its physical form following rehydration for in vivo administration, and will also determine how rapidly the internally entrapped superparamagnetic substance is made available, hydrated, exposed or released, in order that it can modify the biochemical environment of the plasma, extracellular matrix (or matrix water), or intracellular cytoplasmic substituents (or water). Preferably heat stabilization of carbohydrate matrices is performed for about 30 seconds to 5 minutes, in order to render the matrix sufficiently stabilized that the entrapped material becomes chemically exposed over an interval of about 15 minutes to 30 hours. For both the induction of MRI contrast and the amplification of hysteresis heating, the $t_{\frac{1}{2}}$ for release of entrapped agent occurs preferably within about 15-20 minutes of injection, although under certain circumstances, particularly those involving the monitoring of controlled-release drugs from selectively localized microcarriers, this $t_{\frac{1}{2}}$ may be considerably longer. Also, for MRI contrast enhancement, the entrapped material must be hydrated (released) in order to affect surrounding diffusible water protons, whereas, for hysteresis heating, the entrapped material need not be released at all, but can function while still entrapped, providing that the macrodomain size of an average superparamagnetic deposit within the particle is sufficiently large for efficient hysteresis to occur, preferably larger than about 0.5 micron. Otherwise, release of entrapped substituent with subsequent reconcentration by extracellular matrix binding or cellular processes, is preferred in order to achieve an efficient hysteresis response in the tissues.

The smaller particle sizes (of less than 3 micrometers, and especially less than 0.8 micron) are preferred for systemic administration by intravenous injection and for selective arterial administration into critical end-arterial circulations. The larger particle sizes of greater than 5 micrometers, and especially greater than 100 micrometers are preferred for chemoembolization of selected organs with blood supplies, including especially the liver, by selective arterial administration, and for introduction mechanically, directly into tumor masses or body cavities.

The acute enhancement of blood flow (or perfusion) images, for example in the heart or cerebral vessels, may be accomplished with the soluble polymeric image-enhancing agents and is even more efficiently performed with the nanosphere and microsphere forms.

A significant advantage of MRI enhancement with polymeric, nanosphere and microsphere superparamagnetic substance, is a further reduction of the dose and any potential toxicity over that which can be achieved by simple (low molecular weight) superparamagnetic substances alone.

The relatively rapid biodegradation and metal clearance times, and the resultant shorter reimaging intervals are particular advantages involved with the present invention relative to other polymeric and particulate metal oxides, chelates and complexes.

The image-enhancing agents of the present invention, in soluble or microsphere form, are readily reconstituted for animal and patient administration. This reconstitution involves a simple vortex-type mixing, as contrasted with the sonication in detergents used for protein-based microspheres.

The image-enhancing agents of the present invention are easily usable in any MRI detection system involving administration of paramagnetic or ferromagnetic contrast agents. It has particular advantages in conjunction with the newer rapid RF pulse sequences, which reduce native tissue contrast in order to shorten image acquisition times and increase patient throughput. The image or spectral enhancing agents of the present invention allow shorter image acquisition times for satisfactory internal resolutions. These times are generally adequate to produce satisfactory internal images because of the greater enhancement and image contrast produced per unit of superparamagnetic and total agent.

The potential for selective localization of large numbers of relatively nontoxic superparamagnetic molecules by small numbers of monoclonal antibodies, non-peptide and peptide hormones, lymphokines, cytokines, and other receptor-binding substances tagged with one or more of the innovative (and preferably polymeric) image-enhancing agents is contemplated as a major diagnostic advancement for future use.

The potential for selective localization of large numbers of relatively nontoxic superparamagnetic molecules by small numbers of carrier polymers, nanospheres or microspheres is contemplated as a major therapeutic advantage for future use in conjunction with hyperthermia augmentation by hysteresis heating and delivery and monitoring of tagged therapeutic agent localization in sites of disease.

Because of the high MRI contrast conferred by these superparamagnetic substances and the substantial prolongation of lesional residence times, use of the present image-enhancing agents will allow an increased number of serial images to be obtained in an enhancement mode after a single administration of agent.

Due to the selective retention of the carriers used to formulate the present image-enhancing agents, superior definition of tumor margins and markedly improved discrimination of viable and nonviable tumor subregions is possible. This has the major advantage of allowing tumor responses to chemotherapy and radiation therapy to be monitored at early posttreatment times and submillimeter resolution, several weeks before small tumor nodules would regrow to volumes detectible by computerized axial tomography (CAT) and radionuclide scanning.

From a chemical standpoint, some advantages of the present invention may be summarized as follows. When MR image-enhancing agents comprise superparamagnetics, each superparamagnetic substance exhibits an increased relaxivity for adjacent magnetic nuclei (e.g., protons) and hence, gives greater T1 signal enhancement. This increased relaxivity is related to an increased dipolar correlation time of the superparamagnetic substance due to its slower molecular rotation when polymerically controlled. Spacer groups are not required between the superparamagnetic substance and the polymeric carrier in order to obtain optimal paramagnetic relaxation potencies, however, they could be introduced if deemed advantageous for other purposes.

The chemically defined nature of preferred chelator-polymer combinations allows ready batch-to-batch uniformity for improved pharmaceutical formulations and a likely greater ease of regulatory approval.

Many of the preferred polymers of the present invention, such as certain dextrans (40,000 and 70,000 MW forms), hydroxyethyl starch, and heparin, for example, have already separately achieved final regulatory approval for patient administration. The size of these polymers is optimized to prevent access into normal tissues, but to still allow rapid renal clearance and essentially complete body clearance. Also, due to the association of multiple, potent superparamagnetic substances with each polymer molecule, the resulting complexes and conjugates comprise low osmolality agents by comparison to their low-molecular weight counterparts. Such low osmolality agents have been shown to have major advantages in several categories of high-risk (particularly cardiovascular) patients.

For parenteral administration, these agents are preferably formulated as a sterile, physiologically balanced, aqueous solution (or suspension), whose pH for purposes of intravenous administration is 6.5 to 7.0. Alternatively, these agents may be lyophilized and provided in the dried form for reconstitution in physiologic solutions just prior to administration. For injection into body cavities (such as the bladder, uterus, Fallopian tubes, nasal sinuses or ventriculo-cerebrospinal system), these agent may be formulated as a physiological solution (or suspension) which contains additional substances (excipients) to increase the viscosity or osmolality. Other additives and formulations may also be incorporated according to standard pharmaceutical procedures.

For parenteral administration, the concentration of total active agent (polymer-superparamagnetic substance) will be between about 0.1% and 30% (weight/volume), typically between about 5% and 25%, and preferably about 20%. Doses of the soluble polymer, nanosphere and microsphere agents will vary depending on the superparamagnetic substance used and the route of administration. The following doses are given for intravenous administration. For tumor image enhancement with some of the preferred embodiments, which include soluble $Cr_4S(O_2CCH_3)_8(H_2O)_4^{+2}$ complexed to DTPA-hydroxyethyl starch, DTPA-dextrans or heparin, the dose of chromium (and sulfur) will be between about 0.005 and 0.025 millimoles per kilogram of body weight, with optimal image enhancement occurring at or below about 0.01 millimoles per kilogram. For enhancement of the cardiovascular blood pool, the optimal dose of preferred soluble agents will occur at or below about 0.04 and 0.02 millimoles of superparamagnetic per kilogram.

For hysteresis heating, the nanosphere or microsphere forms of agents will be administered once or multiply, at about 15 minutes to 2 hours prior to each treatment by either systemic intravenous injection, direct administration into superficial tumors, or by intra-arterial perfusion, at doses of up to 1.0 mmol/kg of the superparamagnetic substance. Hysteresis hyperthermia at a frequency of about 10 to 150 kHz will be directed from an external oscillating magnetic source whose maximal energy displacement is centered over the major external or imageable mass(es) of tumor. A major anticipated advantage of using the nanosphere or microsphere form of preferred embodiment, is that a high concentration of clustered (macrodomain) metal is selectively localized in the diseased subregions of the target tissue following transvascular administration, and this localized material further concentrates in the viable, most heavily perfused subregions of tumor which require the greatest augmentation of heating to compensate for their disproportionate loss of heat due to blood flow dissipation.

Figure 3:
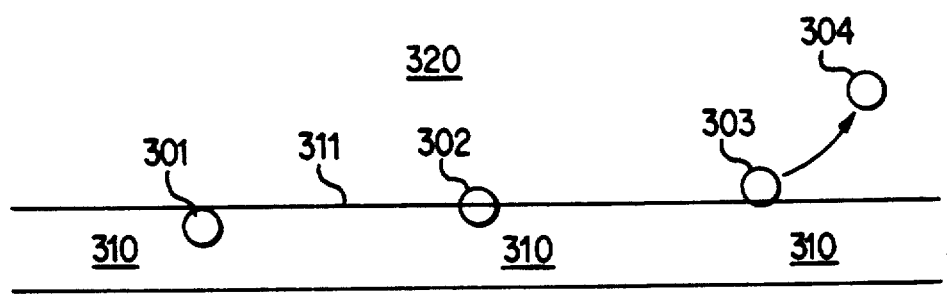
FIG. 3 is a schematic representation of the transport of microspheres entirely across endothelial (or epithelial) tissue.

FIG. 3 schematically shows how the trans-epithelial transport of microspheres works. A small blood vessel 310 is shown passing through tissue 320. Four microspheres (or nanospheres) 301, 302, 303, and 304 are shown at different stages of passage.

Microsphere 301 has recently adhered to the endothelial wall 311. Thus, this microsphere is said to be at the stage of endothelial adhesion.

Microsphere 302 is at the stage of endothelial envelopment. This will occur after a few minutes, as the wall 311 gradually covers a particle (like microsphere 301) which has adhered to it.

Microsphere 303 is shown at the further stage of extravasation, after envelopment has passed it entirely across the endothelial (or epithelial) wall 311.

Finally, microsphere 304 is shown at yet a further stage, of percolation through tissue.

Figure 4:
FIG. 4 is a photograph of stained tissue showing localization of nanospheres. The nanospheres, at the scale of this photograph, appear as small gray round or oval dots of 1 to 2 $\mu m$ in diameter.

FIG. 4 is a photograph of stained tissue showing lung localization of heparin-coated subembolizing (0.1-0.8 micron) nanospheres distributed throughout rodent lung tissue at 5 minutes after intravenous injection via the tail vein. The nanospheres, at the scale of this photograph, appear as small gray round or oval dots of 1 to 2 mm in diameter.

The following examples are presented to illustrate preferred embodiments of the present invention and their use in MR imaging or hysteresis heating. These examples are purely illustrative, and do not in any way delimit the full scope of the present invention.

EXAMPLE 1

Preparation of DTPA-Dextrans

The cyclic dianhydride of DTPA (diethylenetriamine pentaacetic acid), as prepared by the method of Eckelman et al. (J. Pharm. Sci. V 64, pp 704-706 (1975), was obtained in a highly pure form from Calbiochem-Bhering Corp. The completely soluble DTPA derivative of dextran was prepared by adding 7.0 g of the cyclic DTPA dianhydride stepwise to 1.72 g of Dextran T70 (average MW 70,000 Daltons, $M_N$ 46,000, Pharmacia Chemicals) in a reaction solvent comprising HEPES buffer 115 mg/100 cc distilled water, pH 7.0 to 8.0. The reaction was carried out with vigorous stirring at ambient temperatures for 1 hr with readjustment to pH 7.0 using NaOH, after the addition of each aliquot of DTPA dianhydride.

The dextran-DTPA product was separated from unconjugated DTPA by dialysis against 200 volumes of 0.15N NaCl and then 50 volumes of distilled water at pH 6.5. This and the following step are major improvements over the derivatization method previously filed by the present inventor. (See U.S. patent application Ser. Nos. 799,757 and 086,692, and PCT Application PCT/US86/02479, which are hereby incorporated by reference.) Upon completion of dialysis, the conjugate was brought again to 115 mg/100 cc in HEPES buffer, and reacted a second time with an identical quantity of DTPA dianhydride as described above. After this, the dialysis was repeated as described above.

As assessed by molecular filtration, 98% of the dextran-DTPA product had a molecular weight of less than 100,000 Daltons. The dilute solution of DTPA-dextran was either: a) concentrated to between 10% and 25% (w/v) by forced filtered-air evaporation at room temperature, or b) lyophilized to dryness for prolonged shelf storage. Concentrated salts and buffers were added as needed, to render the final preparations physiologically acceptable for injection. The pH was maintained between 6.5 and 7.0. As assayed by complexometric titration, one ligand of DTPA was conjugated for every 7 sugar residues, for a total of 55.5 DTPAs per 389 glucose units in each average molecule.

Two other soluble DTPA-dextran derivatives were synthesized from dextrans of starting molecular weights=10,000 Daltons (Dextran T10, Pharmacia Chemicals) and 40,000 Daltons (Dextran T40, Pharmacia Chemicals). All of the preceding dextrans were soluble and free of microaggregates, as assessed by filtration through serial molecular sieve filters (Amicon Corporation).

EXAMPLE 2

Preparation of DTPA-Hydroxyethyl Starch

Low-molecular-weight hydroxyethyl starch is obtained in a highly pure and soluble form from American Critical Care/DuPont, reacted with the cyclic dianhydride of DTPA, and the polymeric derivative separated, concentrated and titrated as described in EXAMPLE 1.

EXAMPLE 3

Preparation of Succinylated-Dextrans

Succinyl anhydride is obtained in a highly pure form from Aldrich Chemicals, and reacted with dextrans of 40,000 MW and 70,000 MW, and the polymeric derivative separated, concentrated and titrated as described in EXAMPLE 1.

EXAMPLE 4

Preparation of the Paired-Ion Metal
Co-Ordinate-Polymer Complex
Cisplatin-DTPA-Dextran (70,000 MW)

Lyophilized DTPA-dextran (70,000 MW), prepared as in Example 1, was dissolved in 1.4 cc of sterile water, heated for 30 seconds by swirling in a boiling water bath, added (hot) to 70 mg of Platinol TM powder (containing 3.33 mg of cisplatin, $Pt(NH_3)_2$—$Cl_2$ with the remaining weight comprising excipients; Bristol Laboratories), the solution vortexed vigorously for 30 seconds to dissolve the Platinol TM +excipients, and the resulting solution cooled to room temperature and checked for complete solubility at 2.4 mg/ml. Formation of a stable paired-ion complex between the platinum coordinate and the carboxyl groups bound to dextran, was established by three tests: a) continued solubility of cisplatin at a concentration greater than its native solubility limit of 1.5 mg/cc; b) reduction in the complexation of exogenously added calcium ions by the DTPA groups of DTPA-dextran (assessed using an Orion Instruments ionized calcium analyzer); and c) elimination of tetany following intravenous injection of the resulting mixture into CBA/J mice (Jackson Laboratories) at a dose of 10 mg/25 gm body weight. This absence of tetany contrasts with the occurrence of tetany and death in mice which were injected with an equivalent dose of DTPA-dextran alone—and importantly, in the absence of balancing quantities of calcium ion, which render the resulting Ca-DTPA-dextran entirely nontoxic in vivo. Hence, by in vitro and in vivo criteria, cisplatin (as Platinol TM) undergoes complexation to DTPA-dextran at a sufficient binding stability to compete with an added, divalent metal cation ($Ca^{+2}$). The exact coordination state and chemical structure of the resulting cisplatin-DTPA-dextran complex has not been further elucidated.

EXAMPLE 5

Preparation of the Paired-Ion Metal Coordinate-Polymer Complex, Cisplatin-Heparin (22,000–26,000 MW)

Beef lung heparin (Upjohn Company) was added dry at 14 mg to 280 mg of dry Platinol ™ powder (Bristol Laboratories) containing 14 mg of cisplatin, the mixture dissolved in 14 cc of sterile water and vortexed for 1 minute to completely dissolve all components. Formation of a stable paired-ion complex between the platinum coordinate and the sulfate groups covalently bound to heparin, was established by two tests: a) continued solubility of cisplatin at a higher concentration (2.25 mg/cc) than its native solubility limit of 1.5 mg/cc, and b) alteration of cisplatin biodistribution following intravenous and intraarterial injection in animals (see the Examples below).

EXAMPLE 6

Preparation of Heat-Stabilized, Hydroxyethyl Starch-Matrix Nano-Spheres Which Encapsulate Cisplatin and Have a Heparin Surface Coating Hydroxyethyl starch 605 mg (Sigma Chemicals) was suspended in 5.5 cc of sterile water and heated for 3 minutes in a boiling water bath to bring it into a stable (translucent) emulsion, and 5 cc of this was added to 1000 mg of Platinol ™ (Bristol Laboratories) containing 50 mg of cisplatin. This was nanoemulsified for 30 seconds in 70 cc of heated (100° C.) cottonseed oil (Sargent Welch) using a Brinkman Instruments ultrasonic homogenizer, and the oil cooled in a room-temperature water bath, with continued homogenization for 2 more minutes, until the emulsion itself reached room temperature. This was extracted 4 times with acetone (Fisher Chemicals) containing 0.5% Tween 80 (Sigma Chemicals), and was harvested by centrifugation and air dried. The resulting particle diameters ranged from 0.1–1.0 micron.

A heparin coating was applied to the particle surfaces by adding 2 cc of a water solution containing 50 mg of beef lung heparin (Upjohn Company), adding the particle suspension plus heparin to 70 cc of heated (100° C.) cottonseed oil and repeating the emulsification and extraction steps described in the preceding paragraph. The resulting particles ranged from 0.1 to 0.8 micron in diameter. The presence of a heparin surface coating was verified by suspending the particles in normal saline and adding protamine (Sigma Chemicals), a multivalent heparin-binding agent. This produced aggregation and agglutination of the heparin-coated (but not uncoated) particles.

EXAMPLE 7

In Vivo Testing for Selective Lung Localization of the Preceding Preparations Following Intravenous Administration CBA/J mice (Jackson Laboratories) were injected intravenously via the tail vein with a) nanoparticles containing a heparin surface (as in Example 6) and b) soluble heparin-cisplatin complex-es (prepared as in Example 5). At 5 to 15 minutes postinjection, the animals were sacrificed, their lungs removed and fixed with intratracheal buffered formalin, tissue sections cut at 8 microns thickness, and the sections stained using a newly devised method for platinum which comprises a microwave-augmented iron-type stain (60° C. $\times 2$ minute $\times 3$ cycles) using a 1:1 mixture of 2% ferriferocyanide reagent and 4% HCl. By this method, lung uptake of both the nanospheres (see FIG. 4) and soluble paired-ion complex of cisplatin-heparin was documented at the 5-minute postinjection interval. Rapid uptake occurred in both extracellular and intra-cellular compartments, and additional histochemical positivity of bronchial respiratory epithelium and paratracheal lymph nodes was observed at 10–15 minutes. No significant staining was observed following intravenous injection of a standard formulation of Platinol (Bristol Laboratories). To those skilled in the art, additional evidence for selective lung localization, was obtained by injecting intravenously, analogous (subembolizing) heparin-coated nanoparticles containing encapsulated amphotericin B, into identical mice, homogenizing the lungs, and documenting an 8-fold increment in drug levels over native amphotericin B (deoxycholate formulation, Fungizone; Squibb) recovered at 1 to 3 hours postinjection. (See U.S. patent application Ser. No. 07/033,432, and PCT application PCT/US88/01096, which are hereby incorporated by reference.) Hence, the preceding histologic stains correlated with an increment of nearly 1 order of magnitude in selective pulmonary carrier and drug localization.

EXAMPLE 8

In Vivo Testing for Selective Tumor Localization of the Preceding Preparations Following Intraarterial Administration Additional documentation for maintenance of the cisplatin-carrier paired-ion complex in vivo was obtained as follows. Rabbits bearing VX2 carcinomas of the right hind limb were catheterized under fluoroscopic control, and three of the preceding Platinol formulations, as well as standard Platinol, were injected at a constant dose of 15 mg (of cisplatin) per rabbit by selective arterial perfusion over 15 minutes, into the tumor-bearing limb. Animals were sacrificed at 15 minutes, and the tumors and organs were homogenized extracted and analyzed by atomic absorption for tissue platinum concentrations, as shown in Table 1.

TABLE 1

| Platinum content (ng/mg of tissue, wet weight) - Ipsilateral | | | | | |
|---|---|---|---|---|---|
| Agent | Blood | Tumor | Muscle | Liver | Kidney |
| Heparin-cisplatin: | 2.71 | 12.24 | 0.18 | 5.74 | 5.88 |
| DTPA-dextran cisplatin: | 2.14 | 10.81 | 0.29 | 3.47 | 2.92 |
| Heparin-coated hydroxyethyl starch nanospheres of cisplatin: | 2.43 | 14.07 | 0.20 | 4.64 | 5.91 |
| Standard: | 2.36 | 8.40 | 1.09 | 6.09 | 4.09 |

Additionally, histochemical platinum stains were performed on the tumor tissues, as described in Example 7. These stains revealed intracellular tumor-cell (but not normal-cell) platinum in all of the groups in Table 1 except group 4. Moreover, the intracellular staining of tumor cells in groups 1–3 was significantly more intense than the background staining of hemoglobin iron in red blood cells. Since hemoglobin iron is present at a mean corpuscular hemoglobin concentration (MCHC) of about 0.2 molar, these results suggest strongly that tumor cell platinum reaches very high concentrations relative to those achieved with standard Platinol ™. To individuals skilled in the art, this also indicates that selective tumor-cell augmentation of hysteresis heating may be achieved by first administering one or more of the carrier formulations described above, but in stable complexation with a strong superparamagnetic substance which is otherwise too small and uncontrolled to undergo this degree of selective localization.

EXAMPLE 9

Prolonged Enhancement of Human Tumor (Melanoma) Xenografts in Nude Mice, by Paramagnetic Chelate Associated Covalently With Dextran 70

The strong paramagnetic metal ion, gadolinium ($Gd^{+3}$), was chelated stoichiometrically to DTPA-Dextran 70 polymer, whose preparation is described in Example 1, paragraph 2 (improved formulation). Swiss nude mice were inoculated with BRO-strain human malignant melanomas, and these were allowed to grow to a 1-1.5 cm diameter. Moderately T1-weighted MR imaging (TR = 500 msec, TE = 40 msec) was performed in a standard Diasonics ™ medical imager and a 30-cm RF head coil, before and after intravenous injection of equivalent doses of Gd-DTPA-Dextran-70 (0.03 mmol Gd/kg) or Gd-DTPA (0.1 mmol/kg) contrast agent. Gd-DTPA-dextran and Gd-DTPA began to optimally enhance the tumors at comparably short postcontrast intervals of 10 minutes, however, by one hour Gd-DTPA had completely faded, whereas Gd-DTPA-dextran continued to enhance these tumors intensely for longer than 2.5 hours (the cutoff time on imaging experiments). To those skilled in the art, it will be recognized from these results that chelated Gd and small metal coordinates in general, will benefit greatly in terms of potency (by at least half an order of magnitude), tumor selectivity and tumor retention, from covalent conjugation or strong paired-ion association with dextran or including analogous carbohydrate carrier molecules. It will also be recognized that much lower doses of the stronger superparamagnetics (including doses below about 0.01 mmol/kg, versus 0.1 mmol/kg for Gd-DTPA) can be used to obtain effective MRI contrast enhancement; and that much faster, more heavily T1-weighted pulse sequences can be implemented in the presence of superparamagnetic-polymer conjugates or paired-ion complexes.

In the preceding study (see PCT Patent Application PCT/US88/01096), $^{153}$Gd-DTPA-dextran was documented to clear from the blood with a $t_{\frac{1}{2}}$ of about 50 minutes (versus 20 minutes for Gd-DTPA). Total body clearance was almost complete (greater than 96%) by 24 hours. Hence, to those skilled in the art, it will be recognized that strong association of a metal coordinate with a polymeric carbohydrate of predominantly less than 50,000 MW, allows rapid and complete blood and body clearance by predominantly renal pathways.

EXAMPLE 10

Preparation of Paired-Ion Molecular Complexes of $Cr_4S(O_2CCH_3)_8(H_2O)_4^{+2}$ With Negatively Charged Polymeric Carbohydrate Carriers The following negatively charged polymeric carriers are obtained for individual addition and ion pairing to the ferromagnetically coupled paramagnetic cation cluster, $Cr_4S(O_2CCH_3)_8(H_2O)_4^{+2}$ (Exxon Corporation)(see the Bino et al. article cited above): heparin (22,000-26,000 Daltons, Upjohn Company); DTPA-dextrans (40,000 and 70,000 MW parent carbohydrates, derivatized as in Example 1); DTPA-hydroxyethyl starch (50,000 MW parent carbohydrate, prepared as in Example 2); and succinylated-dextrans (40,000 and 60,000 MW parent carbohydrates, derivatized as in Example 3). Each polymer is added as a concentrated aqueous solution, at stoichiometric charge equivalency, or at 50% or 25% of charge equivalency, to a concentrated aqueous solution of $Cr_4S(O_2CCH_3)_8(H_2O)_4^{+2}$ as the chloride salt. Ion pairing is achieved by direct mixing and heating for 1-5 minutes to 100° C. at pH 7, with vigorous stirring. To subfractions of the 25% and 50% mixtures (above) is added a concentrated aqueous solution of N-methylglucamine at quantities sufficient to achieve electrical neutrality. The stability of ion pairing is tested by performing equilibrium dialysis against 200 volumes of 0.15N NaCl and assaying the retained (polymeric) materials for T1 relaxivity (IBM PC20 NMR Spectral Analyzer). Those skilled in the art will recognize from the results of cisplatin complexation to heparin and DTPA-dextran (documented in Examples 4 and 5) that the even more positively charged $Cr_4S(O_2CCH_3)_8(H_2O)_4^{+2}$ counterion of the present example results in an even stronger ion pairing to heparin and DTPA-dextran than the satisfactory (in vitro and in vivo) pairing achieved for the cisplatin metal-amine coordinate documented in Examples 4 and 5.

EXAMPLE 11

Preparation of $Cr_4S(O_2CCH_3)_8(H_2O)_4^{+2}$ Covalently Conjugated to Neutral Polymeric Carbohydrate Carriers The following two neutral polymeric carriers are obtained for individual addition and ion pairing to the ferromagnetically coupled paramagnetic cation cluster, $Cr_4S(O_2CCH_3)_8(H_2O)_4^{+2}$ (Exxon Corporation): dextran and hydroxyethyl starch. Each polymer is added at 50 mg/cc to a saturated aqueous solution of $Cr_4S(O_2CCH_3)_8(H_2O)_4^{+2}$ as the chloride salt, in order to drive the reaction towards conjugation. Reaction is carried out at an alkaline pH of 8 to 10, at 4° C. initially (and at room temperature in another run), with mild-to-moderate heating (including 45°-60° C.) and over 30 minutes to 10 hours (most preferably 1-3 hours) as has been used and documented previously for manufacturing of dextran-iron oxide (Imferon ™, Fisons Corporation—see Cox et al., 208 *Nature* 237 (1965); Cox and King, 207 *Nature* 1202 (1965); and Cox et al., 24 *J. Pharm. Pharmac.* 513 (1972), all of which are hereby incorporated by reference), in order to facilitate formation of the chromate-oxide bond with hydroxyl groups of the dextran or hydroxyethyl starch. The resulting conjugates are dialyzed and tested for stability and NMR T1 relaxivity as described in Example 10. Those skilled in the art will recognize from the Imferon ™ literature and from knowledge that the water protons of $Cr_4S(O_2CCH_3)_8(H_2O)_4^{+2}$ are labile (see the Bino et al. article cited above), whereas the chromium-ion cluster is quite stable, thereby allowing formation of a chromate-hydroxyl bond with neutral carbohydrates which have moderate-to-high stability, thereby generating useful covalent conjugates.

EXAMPLE 12

Preparation of $Cr_4S(O_2CCH_3)_8(H_2O)_4{}^{+2}$ Covalently Conjugated to Polymeric Carbohydrate-Carboxylate Carriers The following three carboxylated polymeric carriers are conjugated individually to the ferromagnetically coupled para-magnetic cation cluster, $Cr_4S(O_2CCH_3)_8(H_2O)_4{}^{+2}$ (Exxon Corporation): DTPA-dextran (prepared as in Example 1), DTPA-hydroxyethyl starch (prepared as in Example 2) and succinylated-dextran (prepared as in Example 3). Trans-esterification conjugation of $Cr_4S(O_2CCH_3)_8(H_2O)_4{}^{+2}$ (as the chloride salt) is carried out by adding the superparamagnetic ion at a saturating concentration individually to the three carboxylated carbohydrates. Reaction is carried out at an alkaline pH of 8 to 10, with mild-to-moderate heating (preferably at 45°-80° C.) and over 30 minutes to 10 hours (preferably over 1-3 hours), as is accepted practice for transesterification procedures (see Morrison & Boyd, Organic Chemistry (1959). The resulting conjugate is dialyzed and tested for stability and NMR T1 relaxivity as described in Example 10. Those skilled in the art will recognize, from the literature on trans-esterification and from knowledge that the water protons of $Cr_4S(O_2CCH_3)_8(H_2O)_4{}^{+2}$ are labile, that formation of the chromium-carboxylate bond with the carbohydrates acetate or succinylate ligands will occur and have sufficient stability for in vivo use, thereby generating useful covalent conjugates.

Figure 1:
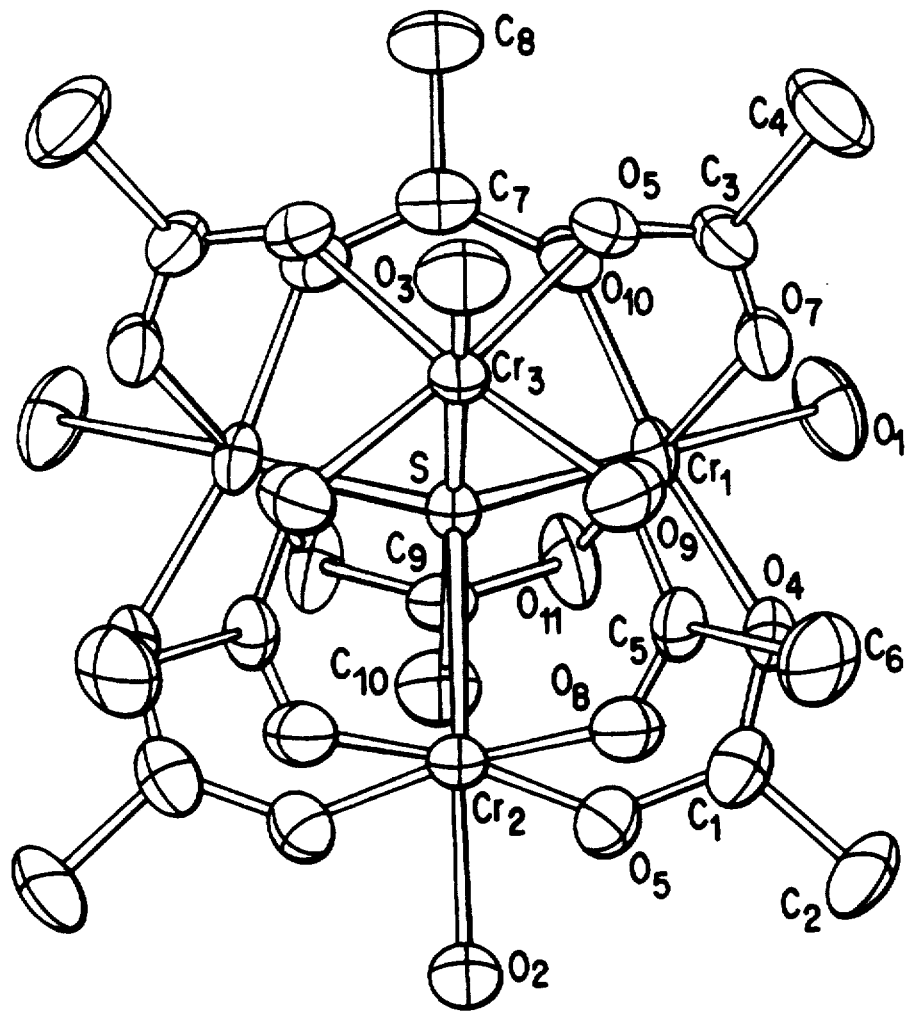
FIG. 1 shows a perspective view of a sample superparamagnetic complex which can be used in one embodiment of the disclosed method.

FIG. 1 shows a perspective view of the $Cr_4S(O_2CCH_3)_8(H_2O)_4{}^{+2}$ cation (excluding hydrogen atoms). The atoms are shown with ellipsoids, to indicate approximate thermal vibration ranges at room temperature.

EXAMPLE 13

Advantages to NMR Imaging of Polymeric Formulations of Super-Paramagnetics, Including Ferromagnetically Coupled Paramagnetic Complexes Selected polymeric formulations of $Cr_4S(O_2CCH_3)_8(H_2O)_4{}^{+2}$, prepared as described in the preceding Examples, are injected intravenously to obtain systemic lesional uptake (frequently practiced in radiology), or intraarterially (less frequently practiced in radiology), to obtain highly selective uptake in regional tumors, especially of the liver, pelvis, brain and limbs. Those skilled in the art will recognize that the more potent, more selective, less toxic (including especially chromium nontoxicity) polymeric formulations of superparamagnetics, including $Cr_4S(O_2CCH_3)_8(H_2O)_4{}^{+2}$ and analogous cluster compounds incorporating ions such as $Gd^{+3}$ or $Fe^{+3}$, advantageously allow the dose of paramagnetic, including chromium, to be reduced to less than about 0.005 to 0.01 mmol/kg of body weight. (See Ranney, *Contrast Agents in Magnetic Resonance Imaging*, in Excerpta Medica at page 81 (1986), which is hereby incorporated by reference). It will also be recognized that MRI procedures involving fast imaging (see Bluem et al., 157 *Radiology* 335 (1985), which is hereby incorporated by reference) and cardiovascular MRI (including MRI "angiography") (see Nagler et al., 157 *Radiology* 313 (1985), which is hereby incorporated by reference) will benefit greatly, in terms of shortened image acquisition time and improved quality, from a nontoxic contrast polymer of super-paramagnetic potency. Additionally, the polymeric superparamagnetic labels described in the preceding Examples are useful for co-labelling either therapeutic drug carriers (polymeric or nanospheric) or the therapeutic agents themselves, whose tumor (or other lesional) localization needs to be monitored and whose rate of release from the carrier (bioavailability) needs to be assessed noninvasively in vivo, potentially in multiple lesions at different depths within a body region. In this context, polymeric superparamagnetic labels are useful and of improved utility due to increased potency and selectivity, and reduced toxicity. Furthermore, increased potency allows drug release to be monitored over longer postinjection intervals within target tissues, organs, tumors and infection. These improvements are based on the present application, and also, in part, on applicant's earlier-reported work on the use of partially analogous, but less potent, Gd-DTPA-dextran-labelled drug carriers leading to localization in tissues and enhanced MRI detection. (See the Ranney and Huffaker article at 507 *Proc. NY Acad. Sci.* 104 (1987), which is hereby incorporated by reference.)

EXAMPLE 14

Advantages to Hysteresis Heating of Polymeric Formulations of Super-Paramagnetics, Including Ferromagnetically Coupled Paramagnetic Complexes Microinhomogeneities of tissue heating represent a major problem in hyperthermia treatment of tumors. This results in considerable part, from the selective survival of tumor cells lying adjacent to microvessels—in which heat loss is accentuated by blood flow. A partially effective approach to this problem has been to inject small ferromagnetic particles of $Fe_2O_3$ directly into the tumor masses, and then apply magnetic hysteresis heating at frequencies of 10-100 kHz to the entire local region. (See Borelli et al., 29 *Phys. Med. Biol.* 487 (1984). Effective superheating and tumor regression in mice occurs if the injected magnetic material is present 1) in sufficient quantity and 2) at a sufficient macrodomain size for efficient hysteresis augmentation to occur (including 0.5-2 micron particle diameters). Because the carrier/ion-cluster agents described in the preceding Examples have the properties of markedly improved selectivity and dose of tumor localization, retention in the viable (perfused) subregions of tumor, and improved tumor-cell uptake, it will be understood by those skilled in the art that these carrier/ion-cluster agents can be of significant benefit in augmenting the homogeneity, magnitude and tumor-cell selectivity of hysteresis heating induced by oscillating magnetic fields, provided that the associated superparamagnetic agents (which may be associated by conjunction, ion-pairing, or encapsulation) become concentrated as adequately sized macrodomains (of at least about 0.5 micron) in the target sites or cells. Histologic staining for cisplatin (per Example 7) of the VX2 rabbit carcinomas which were perfused with heparin-coated cisplatin-hydroxyethyl starch nanospheres (of 0.1-0.8 micron diameters), documented that many of the tumor cells in the target region addressed by selective arterial perfusion, stained intracellularly in a punctate pattern, wherein the diameters of punctate staining positivity ranged from 0.1 to 0.8 micron (=the diameters of the original particles). Importantly, high (including about 0.2 molar) intracellular concentrations of cisplatin were achieved in the VX2 carcinoma cells in vivo (see Example 8). The combination of these high levels plus intracellular aggregation were achieved by administering the cisplatin formulated as a heparin-coated microparticle. This documents the type and extent of intracellular accumulation and aggregation of superparamagnetics which are useful in locally amplifying exogenous hysteresis heating. Notably, aggregated staining was absent following intraarterial perfusion of standard (soluble, low-molecular-weight) cisplatin. Hence, in the present example, heparin-coated $Cr_4S(O_2CCH_3)_8(H_2O)_4^{+2}$ hydroxyethyl starch nanospheres and microspheres of 0.8–3.0 micron diameters, when administered intraarterially, are useful as amplifiers of hysteresis heating, and therefore as inducers of augmented cell death in vivo.

EXAMPLE 15

Glycine-Substituted New Polyatomic Cr Cluster

Figure 5A:
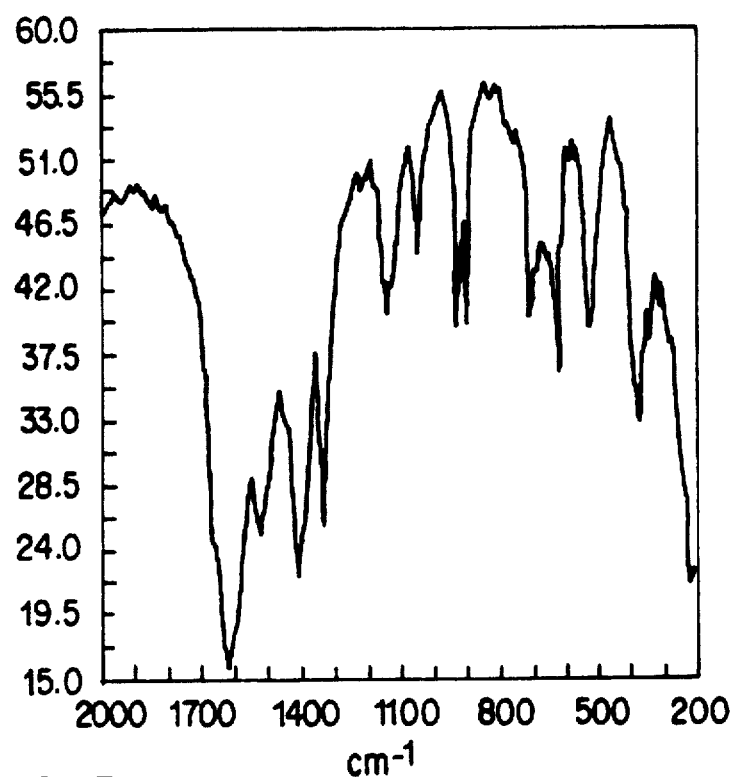
FIGS. 5A-5E show infrared data pertinent to the fabrication of a further alternative superparamagnetic complex, which can be used instead of that shown in FIG. 1.
Figure 5B:
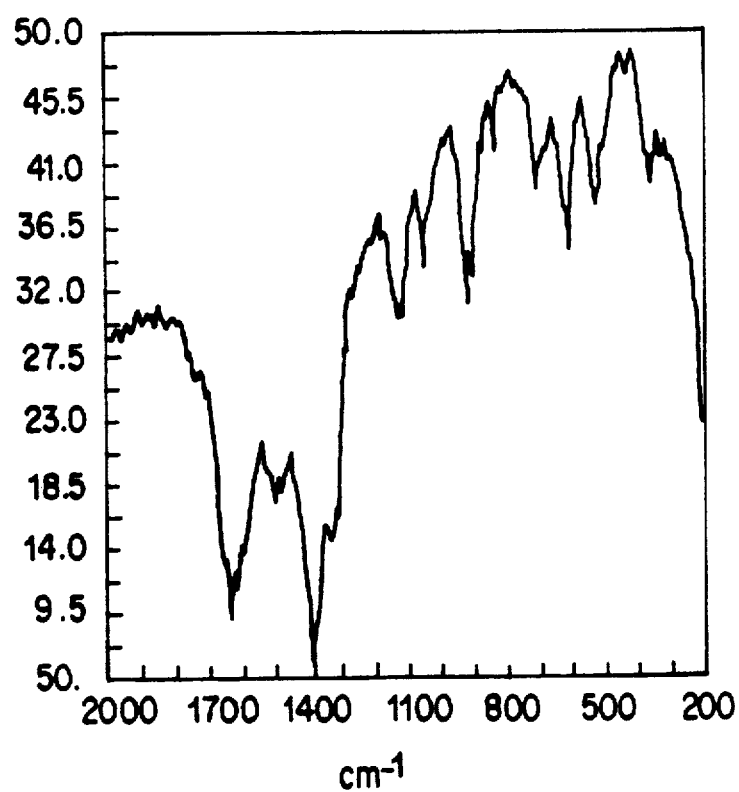
Figure 5C:
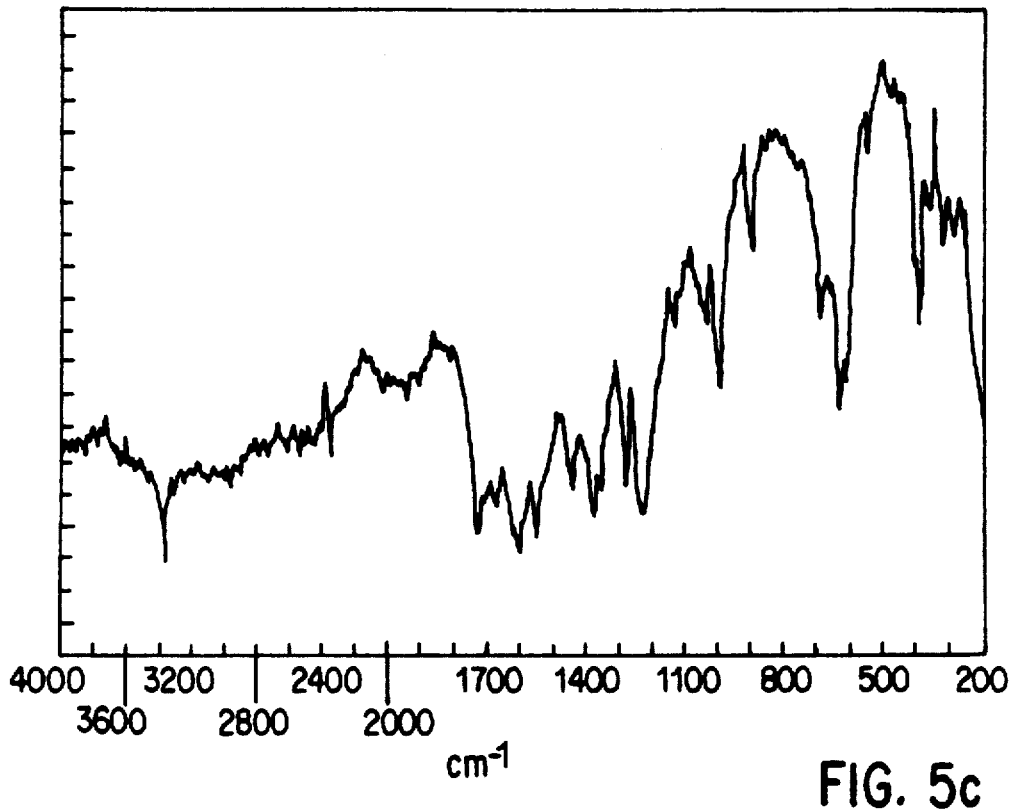
Figure 5D:
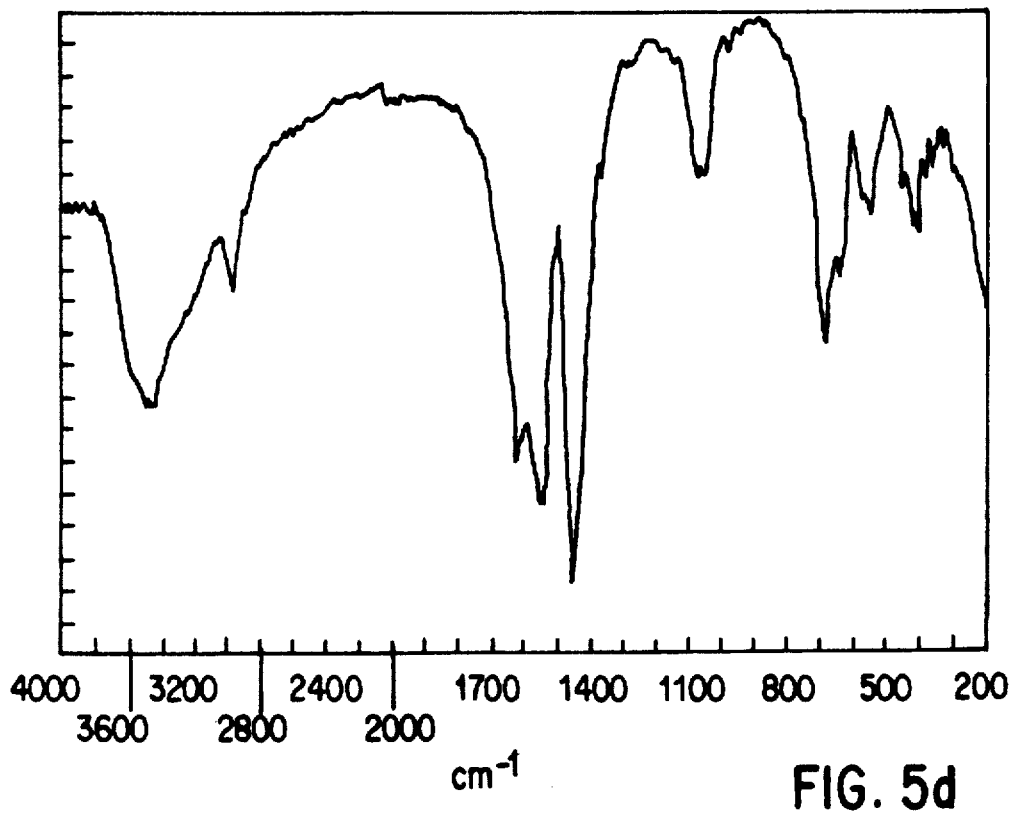
Figure 5E:
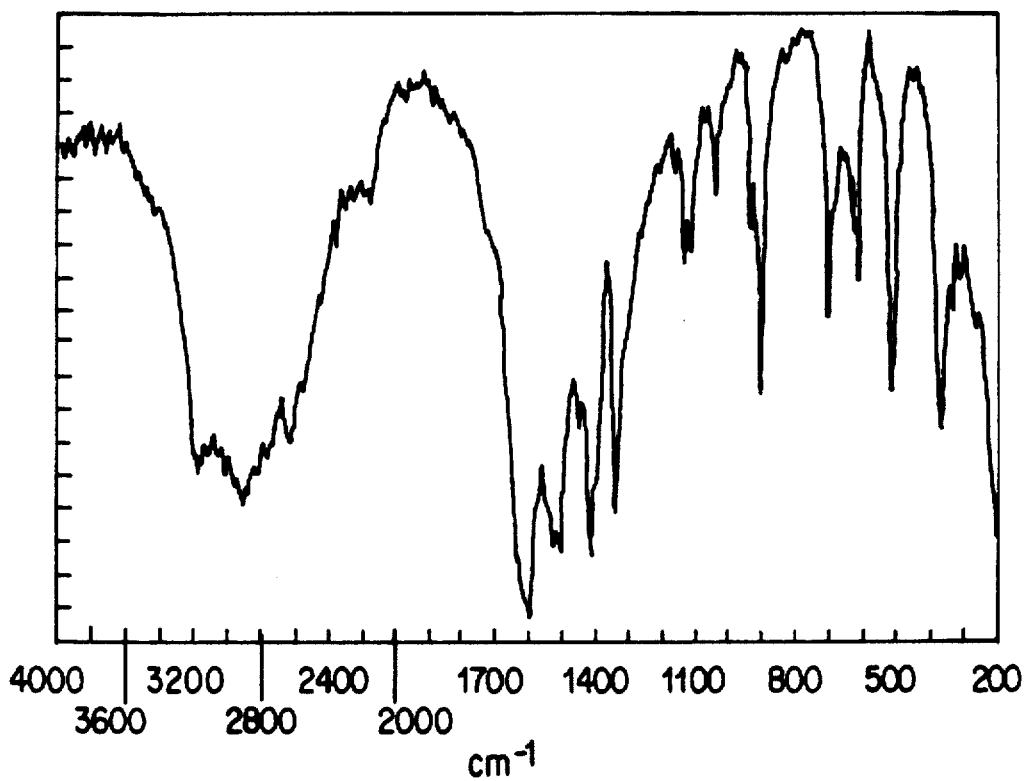

The substrate, $Cr_4S(O_2CCH_3)_8(H_2O)_4$, was prepared as described by A. Bino et al. (*Science*, Vol. 241, pp. 1479–1482, Sep. 16, 1988). This was added at 0.5 gm to 50 cc of acetic anhydride, followed by the addition of 0.1 gm of glycine. The mixture was refluxed at 142 degrees C. for 4 hours, resulting in a yellow-green solution which was poured while still hot into cold water. Evaporation of the solvent gave yellow crystals, which, when recrystallized, gave an infrared (IR) spectrum indicative of glycine substitution for some of the acetate bridging groups, and retention of Cr—O and Cr—S bonds (FIG. 5C, with FIGS. 5D and 5E representing the appropriate controls). Specifically, the IR bands around 1600 $cm^{-1}$ (FIG. 5C) are characteristic of ionized bidentate glycine, and the bands between 300 and 400 $cm^{-1}$ are also consistent with this. The additional bands between 300 and 400 $cm^{-1}$ are also consistent with the presence of Cr—O and Cr—S bonds. FIGS. 5A and 5B show the degradation controls wherein the $Cr_4S(O_2CCH_3)_8(H_2O)_4$ degrades to ionic chromium (by IR spectral criteria) when heated with glycine in an aqueous (protonating) solvent, water, for 4 hours at 92 degrees C. These results provide strong evidence for the formation of a novel polyatomic chromium-atom cluster compound of the general formula, $Cr_nS(O_2CCH_3)_x(Gly)_y(H_2O)_z$, wherein n is the number of Cr atoms greater than 1, x is the number of acetates between about 3 and 7, y is the number of glycines between about 1 and 5, and z is the number of loosely bound waters. The inclusion of bidentate glycine as a new bridging ligand in the polyatomic chromium cluster provides a new reactive (charged) group for binding to carriers and renders the entire compound new and novel.

EXAMPLE 16

New Polyatomic Gadolinium Cluster Compound

Gadolinium chloride (3.7 gm, Alpha) and $Na_2S$ (2.4 gm, Sigma) were mixed in 25 cc of a 1:1 mixture of glacial acetic acid and acetic anhydride and refluxed at 138 degrees C. for 3 days. After removal of the dark red, gadolinium-negative filtrate, a lightly tan-colored precipitate was recovered which was qualitatively positive for gadolinium and which, after recrystallization, yielded a water-soluble water-stable compound whose IR spectrum was consistent with gadolinium acetate. Importantly, several additional bands were present in the carbonyl (ca. 1500 $cm^{-1}$) and C—O (ca. 1000 $cm^{-1}$) bond stretching wavelengths, which are strongly indicative of a polyatomic (polymeric) nature of this complex and, hence, indicative of a novel, gadolinium-containing, polyatomic complex for use with the disclosed carriers.

EXAMPLE 17

Formation of Stable Carrier/Polyatomic Metal Atom Complexes

Carboxymethyl dextran was obtained commercially and mixed with $Cr_4S(O_2CCH_3)_8(H_2O)_4$. The resulting complex had a T1 relativity (R1) 3 times greater than that of the simple chromium cluster, indicative of strong paired-ion binding between the chromium cluster and the carrier. Analogous mixtures were performed of $Cr_4S(O_2CCH_3)_8(H_2O)_4$ and (a) dicarboxyethyl dextran; (b) heparin; and (c) dextran sulfate. The resulting paired-ion complexes were stable to dialysis in 0.15 molar (isotonic) to 0.5 molar saline.

EXAMPLE 18

Imaging Data

Preparation of $(Cr_4S(O_2CCH_3)_8(H_2O)_4)$-heparin carrier (hereinafter "Cr$_4$S-heparin") for in vivo Magnetic Resonance imaging Two aliquots of the Cr$_4$S ion cluster (37.5 mg each) were dissolved in 1 ml (each) of 5% dextrose in water. To the first aliquot was added 187.5 mg of dextran sulfate carrier (8000 Daltons); and to the second aliquot was added 187.5 mg of beef lung heparin carrier (ca. 16000–18000 Daltons). Each aliquot (mixture) was tested for stability of Cr$_4$S-to-carrier binding, by nitrogen pressure ultrafiltration through an (Amicon Corporation) YM10 (1000-Dalton cutoff) filter, followed by washing with 5% dextrose in water. Almost complete retention of the (intensely blue-colored) Cr$_4$S ion cluster above the filter (i.e. in the retentate of more than 10000 Dalton m.w.) was achieved by the heparin carrier. This indicated stable complexation binding of the Cr$_4$S ion to heparin in the presence of 834 milliosmolar dextrose (equivalent to 0.42M NaCl). Hence, the Cr$_4$S-heparin agent remained stably bound (complexed) under conditions equivalent to severe pathologic hyperglycemia (almost incompatible with life) and under conditions of lethal hypernatremia. Retention of Cr$_4$S above the filter was also observed with the dextran sulfate carrier, but was not as complete as in the presence of heparin. This partial retention in the presence of dextran sulfate carrier may be due to the close proximity of the combined molecular weight of Cr$_4$S-dextran sulfate carrier (ca. 10000 Daltons) to the retention cut-off value of the YM10 filter (10000 Daltons).

Acute Toxicity testing in vivo

The Cr$_4$S-heparin preparation (prepared as described in the preceding paragraph) was injected as an intravenous bolus into male CBA/Ln mice at ca. 3000 mg/kg, and the animals were observed for signs of acute toxicity. The animals tolerated this dose of the preparation well immediately after injection, and were also alive, active and gaining weight normally at 1 week post-injection.

Production of Cr$_4$S-heparin for in vivo imaging

The Cr$_4$S ion cluster was allowed to stably complex with heparin at its stoichiometric binding ratio of ca. 30–35% (w/w) Cr$_4$S to heparin (equivalent to about 5.4%–6.3% total chromium content (w/w to heparin). This was tested for T1 relaxivity (R1) using an IBM PC20 relaxometer (IR rf pulse sequence), and gave a 50% decrease in the water proton relaxation time at a concentration of ca. 0.33 to 1.0 mg/ml of total agent (Cr₄S-heparin).

In Vivo MRI of tumor-bearing and control mice

The Cr₄S-heparin MRI contrast agent (from the preceding paragraph) was injected at 0.08 mmol/kg (of Cr₄S ion cluster) into Balb/c mice bearing a well-differentiated, slow-growing, malignant breast tumor induced in the mouse's lower right breast pad. Control animals consisted of uninjected normal mice and normal mice injected with Cr₄S-heparin.

Specifications of MR imager, imaging conditions, and image processing methods from MRI tests of murine breast tumor, enhanced with chromium ion cluster-heparin complex (Cr₄S-heparin)

Transaxial images were acquired simultaneously on three lightly anesthetized (i.p. pentobarbital) mice, using a standard clinical Diasonics whole-body, 0.35 Tesla MR imager, with the three mice oriented in the prone position, facing forward in the magnet and located centrally within a 20-cm radio frequency coil (standard knee coil). High resolution images were acquired over 2.6 minute intervals, both precontrast and at several postcontrast times between 10 and 30 minutes, at an in-plane resolution of 0.9×0.9 mm and a slice thickness of 5 mm. Five contiguous slices were acquired and the optimal slice photographed for maximal cross-sectional assessments of tumor, liver and kidney.

A pulse-sequence optimization program was run on the mice in the region of tumor, ranging from T1-weighted (TR=125 msec) to T2-weighted (TR=1800 msec) spin-echo sequences. The optimal spin-echo conditions were: TR of between 250 msec and 500 msec at an echo time (TE) of 40 msec. Based on these results, a spin-echo pulse sequence was used of TR=325 msec and TR=40 msec. (Note that optimization of contrast enhancement under these T1-weighted spin-echo conditions has two important implications:

1) the Cr₄S-heparin agent behaves as a "T1" contrast agent; and
2) the Cr₄S-heparin agent is optimal for use with the more commonly employed, higher signal-to-noise clinical T1 pulse sequences.

Quantitative changes in tumor image intensities in vivo, at 10 and 30 minutes after intravenous injection of contrast agent (Cr₄S-heparin) at a dose of 0.08 mmol/kg (based on chromium-ion complex) were assessed in the following standard fashion:

1) The average image intensity of central tumor region was acquired (from 64-80 image pixels each) by drawing a cursor box around the comparable central regions of tumor at precontrast, 10-minute post-contrast and 30-minute postcontrast times. (NOTE: Refer to the second, lighter grey scale, 35-mm projection slide of tumor for the exact positioning of the cursor box (this appears as a dark, irregular, rectangular-oblique line over the right-hand flank of the mouse, directly below the bright external stick-marker which was taped to the mouse skin at the site of the tumor. See FIG. 6 and Table 2.)

2) The average image intensity of vertebral muscle was acquired identically (from 20-64 image pixels each). (Note: in FIG. 6, note the positioning of the smaller, dark square cursor boxes located centrally and at the top (dorsum) of each mouse (in the pre, 10-min postcontrast and 30-min postcontrast panels). See FIG. 6 and Table 2.)

3) Any potential artifacts in the postcontrast intensity of breast tumor which might be introduced by changes in the overall intensities of the postcontrast versus precontrast images are corrected (normalized) by the standard method (accepted experimentally and clinically), of forming the mathematical ratio of tumor-to-vertebral muscle image intensities at each imaging time (pre, 10-min post, and 30-min post). (See Table 3, which is derived from Table 2.)

Specifications of NMR Relaxometer, relaxation conditions, and data acquisition for in vitro confirmation of tumor T1 relaxation time and pre-to-postcontrast differences in liver and kidney T1 relaxation times At 40 minutes after injection of contrast agent, the exact animals imaged above were sacrificed, the tumor and organs removed and the T1 relaxation times were determined using an IBM PC20 Relaxometer (operating at 20 MHz), using a T1 inversion-recovery, 180 degrees+90 degrees radiofrequency pulse sequence. (See Table 4.)

The raw data are expressed as the means of 3 to 5 individual measurements made on each organ (or tumor). The processed data are expressed as the "percent of Control" organ T1 (which is the "B" Uninjected Control animal). (Please note: A difference of about ±7% is significant for each value. Hence, the decreases in kidney T1's are highly significant for both of the injected animals ("A" and "C"), but the liver T1's of these same animals are not significantly different from the uninjected control animal ("B"). Note also: Changes in the in vitro T1 relaxation times are inversely related to changes in the in vivo image intensities (enhancement of organs and tumor) at small to moderate percentage changes where T1 effects predominate and T2 effects are minor (typically at T1 percentage decreases less than about 30-40%).

In Vivo Tumor Imaging Results

Figure 6A:
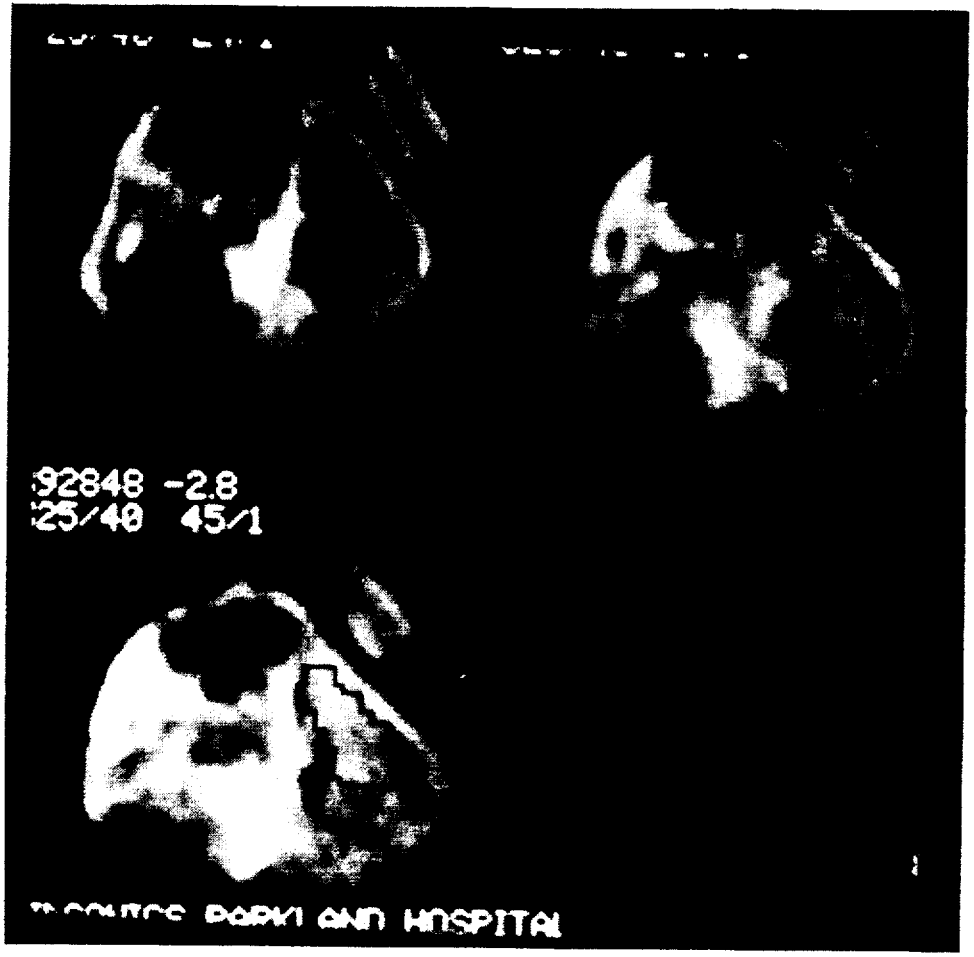
FIG. 6A shows in vivo magnetic-resonance imaging of solid tumors in tumor-bearing mice, recorded in accordance with a sample embodiment of the novel imaging methods set forth herein.
Figure 6B:
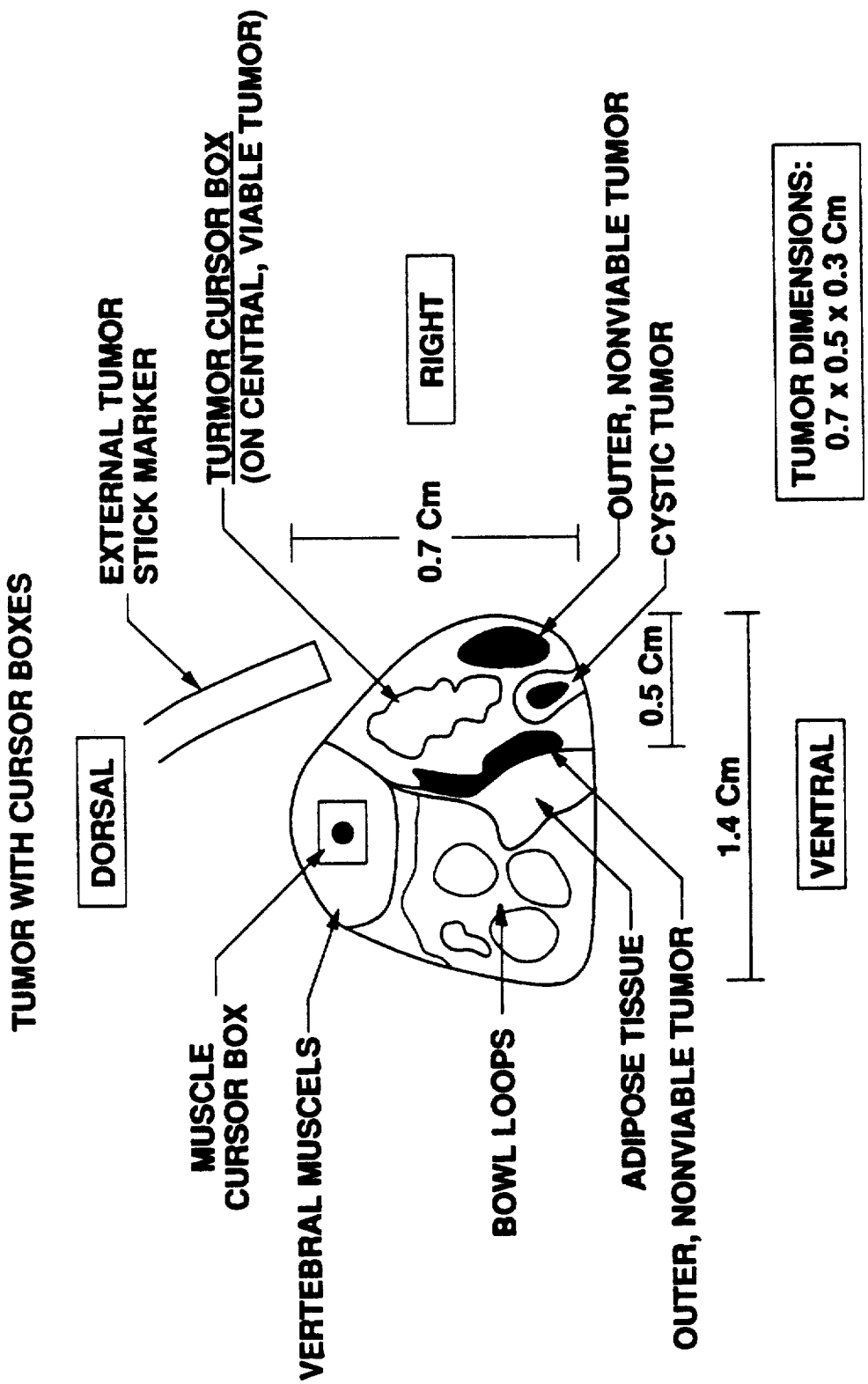
FIG. 6B is a corresponding sketch to assist in the interpretation of that image.

FIG. 6, which shows tumor mass in right flank, with the label of image slice "45/1" on the lower left-hand image panel, and the stick marker located just dorsal to the tumor and cursor boxes located centrally within tumor mass (at image right) and centrally within vertebral muscle (at image top). (The tumor map further clarifies orientation and dimensions.)

1) Precontrast: The entire tumor mass has an intermediate (grey) appearance which is relatively homogeneous. (Refer to Table 2 for the absolute values of tumor and muscle intensity.) The ratio of tumor/muscle intensity (within the cursor boxes) is 1.51/1. (SEE Table 3.)

2) 10 minutes Postcontrast: The central core of the tumor mass (circumscribed by the cursor box) has increased markedly in absolute intensity, whereas the vertebral muscle has not (Table 2). The increment in central tumor intensity is such that the tumor/muscle ratio has increased to 1.98 (or by 31%). Substantial tumor architecture is now seen which was not visualized in the precontrast image (with this T1-weighted sequence—TR=325 msec; TE=40 msec) or any other of the pulse sequence tested—see above). The outer rim of tumor, both medial to the bottom of the cursor box, and at the lateral right border of tumor (just to the right of the bottom of the cursor box) are significantly darker than the central core. Also, a darker cystic structure with a surrounding brighter rim is present immediately below (ventral to) the bottom of the cursor box.

CORRELATION: On gross histologic examination, the three darker regions corresponded to necrotic regions of tumor, and the bright central regions corresponded to viable tumor with more extensive microvascularization.

3) 30 minutes Postcontrast: The same enhancement of tumor subregions is observed as at 10 minutes postcontrast. NOTE: The overall image intensity is slightly brighter at 30 minutes versus 10 minutes; however, as assessed by muscle intensity ratios, the muscle increment at 30 minutes is very slight (4% brighter based on absolute muscle intensity ratios of 3003/2896). Notice also that the external stick probe is visually of about the same intensity from precontrast to 30 minutes postcontrast.

NOTE: By visual inspection, the range of image pixel intensities in the central core of tumor (cursor boxes) is narrower at 10 minutes postcontrast than at 30 minutes postcontrast. This correlates with a lower standard deviation of tumor image intensity by quantitative pixel analysis at 10 minutes postcontrast (Table 2, line 2) than at 30 minutes postcontrast (Table 2, line 3).

Renal and Hepatic Data

Figure 7A:
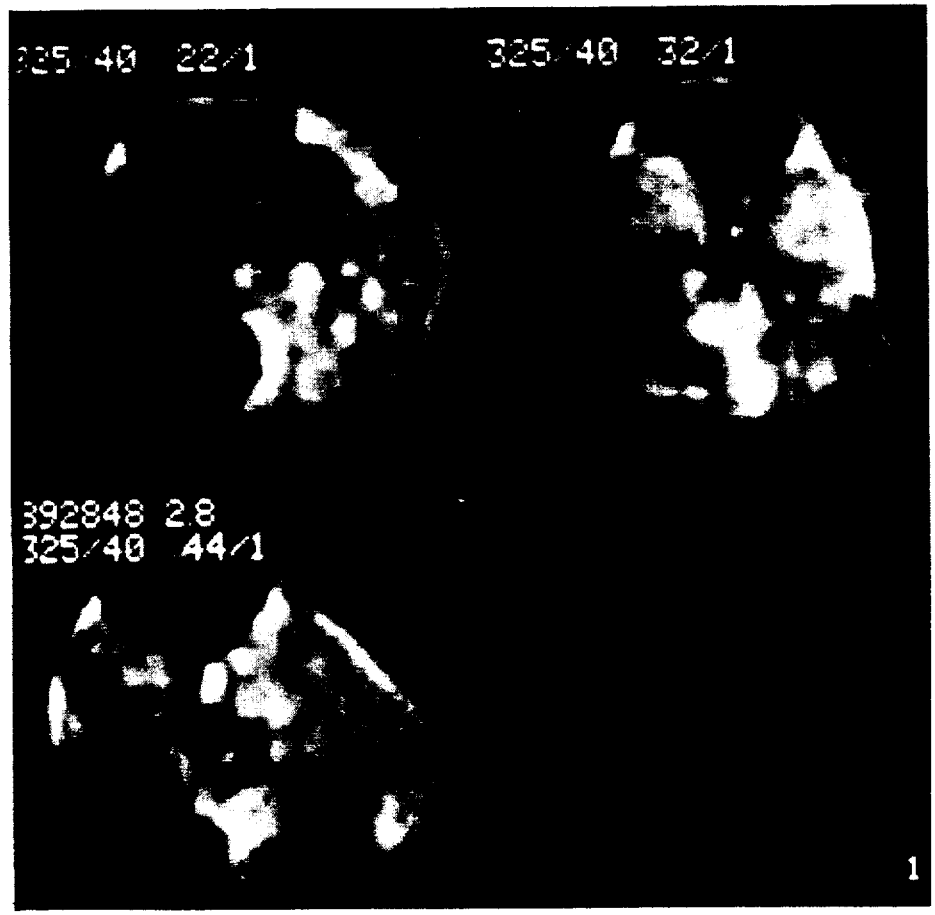
FIG. 7A is a magnetic-resonance image of kidneys in the mice of FIG. 6A.
Figure 7B:
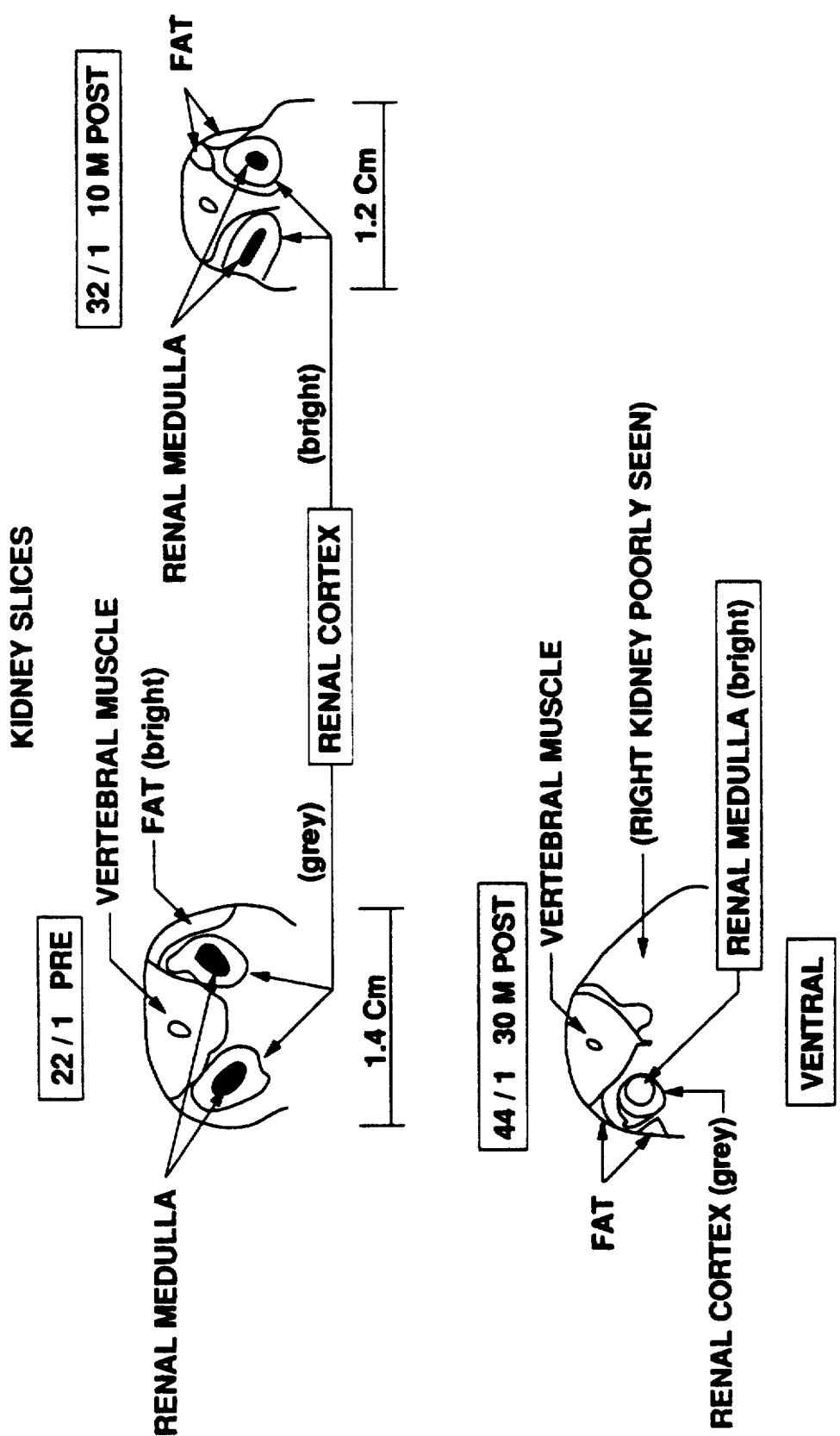
FIG. 7B is a corresponding sketch to assist in the interpretation of that image.

FIG. 7 shows the renal image slices, marked 22/1, 32/1 and 44/1, respectively at the precontrast, 10-min postcontrast, and 30-min postcontrast intervals.

1) Precontrast: The faint outlines of both renal cortices appear as intermediate (grey) intensity oval outlines which are located immediately ventral and slightly lateral to the dorsal vertebral muscle, and which circumscribe the darker (black) central renal medullas.

2) 10 minutes Postcontrast: The image intensities of renal cortical regions are markedly increased in intensity, with the medullary regions being relatively darker although still absolutely increased.

3) 30 minutes Postcontrast: The image intensity of left renal cortex (the left kidney is the only one which is clearly seen in this postcontrast image) has decreased markedly relative to the 10-minute postcontrast time, but remains slightly brighter than the precontrast intensity. Conversely, the left renal medulla (central region of the left kidney) is quite intense, indicative of continued contrast accumulation in the renal collecting system.

Figure 8A:
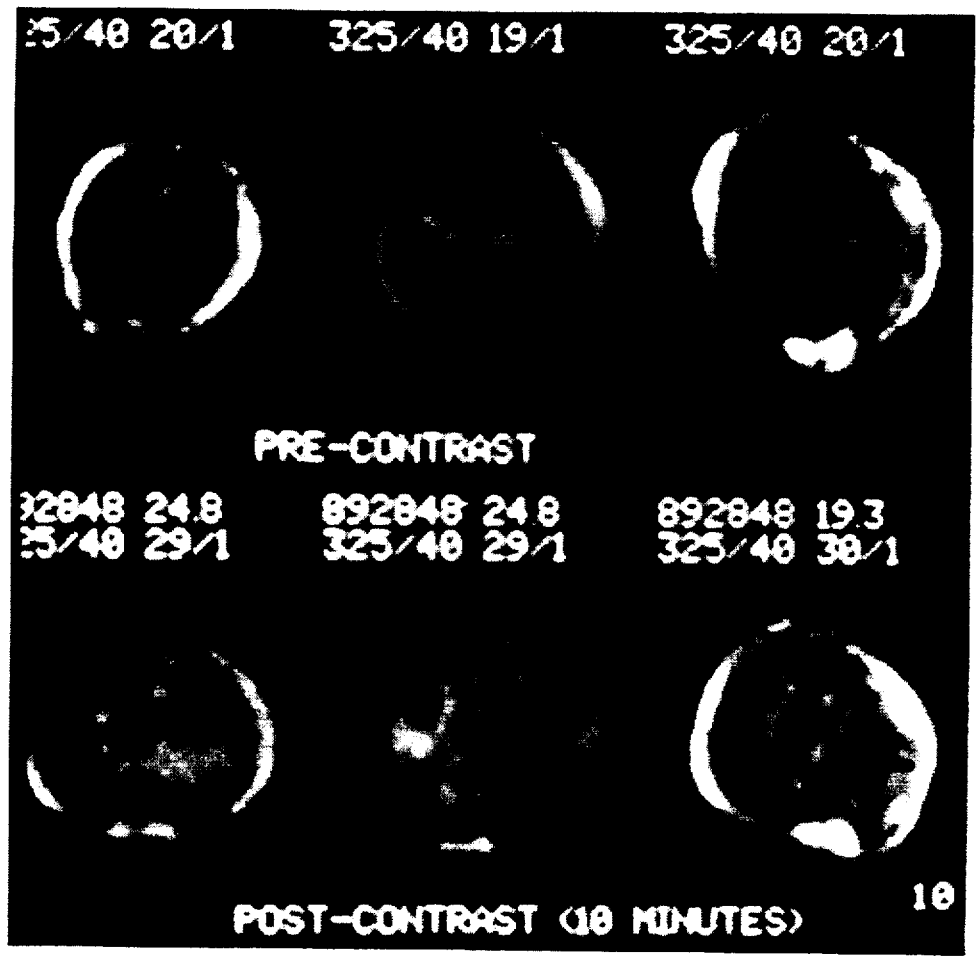
FIG. 8A is a magnetic-resonance image of livers in the mice of FIG. 6A.
Figure 8B:
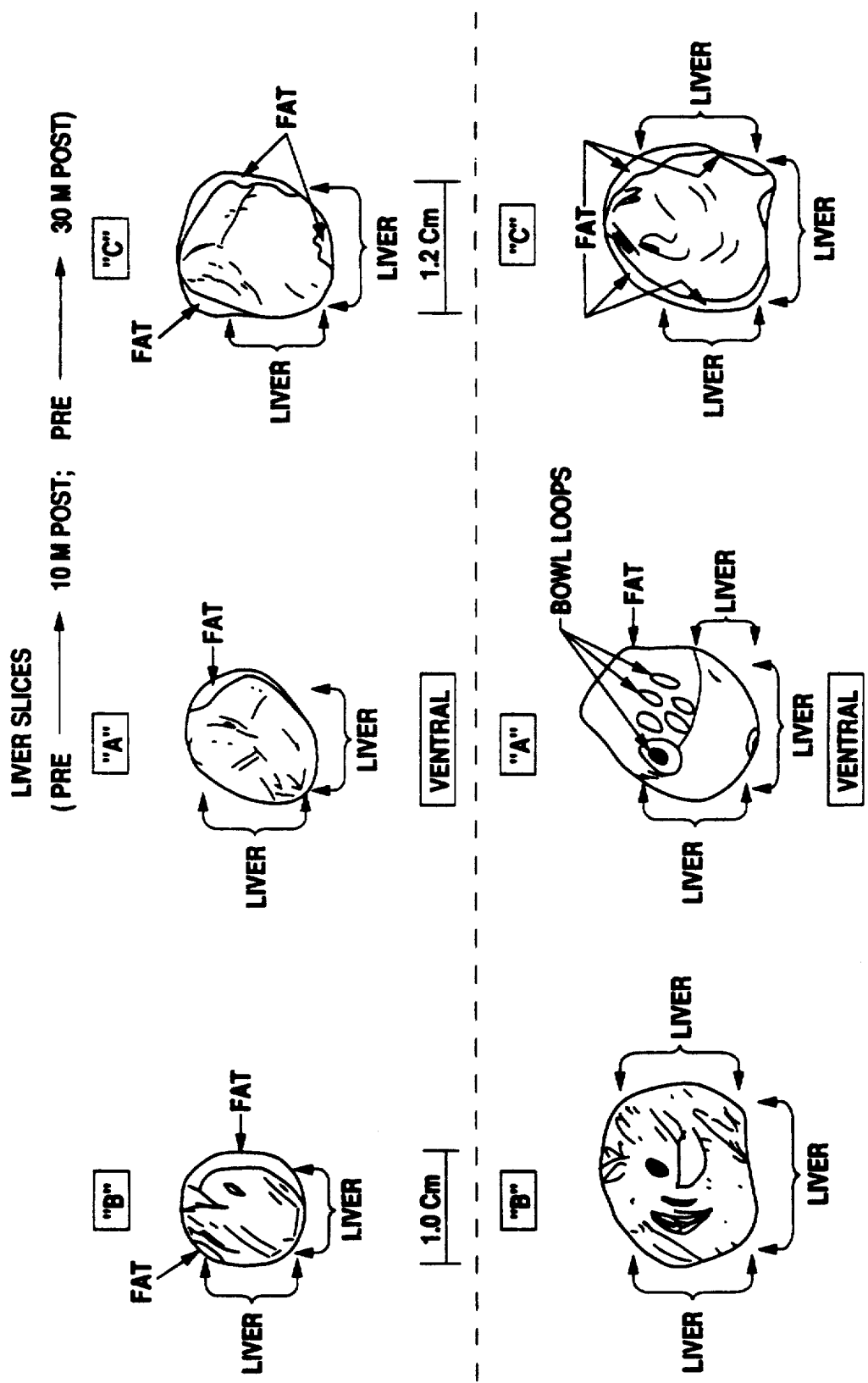
FIG. 8B is a corresponding sketch to assist in the interpretation of that image.

FIG. 8 shows a panel of 6 liver slices—3 top and 3 bottom—at precontrast, and 10-minute postcontrast intervals.)

1) Precontrast livers are viewed in the upper row images as relatively homogeneous, intermediate-intensity (grey) masses which fill almost the entire internal abdominal volume of each mouse. The darker tube-shaped regions are larger hepatic veins and the occasional brighter regions are hepatic septae and omental fat due to caudal volume averaging (see below). The liver image of the left-hand mouse (upper row) is positioned slightly cephalad (superior) to the optimal position for liver imaging, as indicated by the slight decrease in body width. The darker intensity of this precontrast image (relative to the other five livers) is due to slight partial volume averaging with the adjacent lung fields (which, if imaged alone, would appear black).

2) Postcontrast livers of the identical animals appear in the bottom row, as follows:

a) left-hand animal (mouse "B") is contrast-injected ($Cr_4S$-heparin at 0.08 mmol of $Cr_4S$/kg) normal (nontumor) control mouse.

b) middle animal (mouse "A") is an uninjected normal control mouse.

c) right-hand animal (mouse "C") is a tumor mouse injected with 0.08 mmol/kg of $Cr_4S$-heparin contrast agent.

NOTE: In an optimal 5mm-thick image slice, the liver appears relatively homogeneous and of intermediate (grey) image intensity. At both 10-minute (not shown) and 30-minute (not shown) postcontrast times, dark loop densities (bowl loops) and occasional small bright nodules and ring structures (omental fat) are seen in the liver slice of the middle "A" mouse. This is not due to contrast agent (none was injected into this mouse), but is due, instead, to slight caudal mispositioning (and, hence, volume averaging) of the liver image slice. A similar but less prominent artifact is present in the left-hand "B" mouse. Minor volume averaging of this type is usually present in a multi-animal experiment because the mouse liver is only about 5 mm in average height.

OVERALL RESULT: There is no significant image enhancement of liver in either of the injected mice (left "B"; or right "C") at either earlier (10-minute—shown) or later (30-minute—not shown) postcontrast times at which images were acquired.

Preliminary Conclusions

Based on the further experimental data just described, some additional conclusions appear to be justified:

1) Enhancement of a difficult (relatively differentiated) breast carcinoma occurs acutely (10 minutes) after a low (0.08 mmol/kg) dose of the $Cr_4S$-ion cluster-heparin complex.

2) This enhancement persists for an extended, 30-minute post-contrast interval and is not significantly decreased at 30 minutes.

NOTE: This preservation of postcontrast enhancement is markedly longer than the contrast enhancement resulting from Gd-DTPA dimeglumine (MAGNEVIST, Schering AG-Berlex) which undergoes almost complete fading (tumor clearance) by 30 minutes postcontrast.

3) Maximal image enhancement occurs in functionally viable (perfused) tumor subregions; and minimal enhancement occurs in necrotic subregions.

4) Systemic clearance of the $Cr_4S$-heparin MRI contrast agent is predominantly by the renal route and occurs relatively quickly (first, major component requires about 30 minutes—as evidenced by the brightening and then fading of the renal cortex, with continued moderate contrast intensity in the renal medulla at 30 minutes).

5) Importantly, no major acute uptake occurs into NORMAL liver during optimal postcontrast imaging intervals.

Interpretation and Implications.

1) Although the $Cr_4S$-heparin contrast agent contains four Cr ions per ion complex in a superparamagnetic orientation (and, hence, exhibits intracomplex magnetic coupling), in vivo pulse-sequence tests indicate that this contrast agent acts as a potent T1 agent. in vivo dose-efficacy results indicate that this is a highly potent agent. This result suggests that the agent has a more selective initial biodistribution compared to the existing small-molecular contrast agents (e.g., MAGNEVIST and Gd-DTPA, which exchange freely into ca. 35% of total body water and into most of the extracellular fluid, ECF).

2) Following i.v. injection, the $Cr_4S$-heparin agent becomes sequestered rapidly in tumor interstitium but not in normal liver interstitium or parenchyma. This unique property provides for optimal body (as well as brain) imaging of tumors (including tumor within the liver) as well as potentially other body lesions (hepatitis and inflammatory/infectious lesions).

3) Tumor retention of contrast agent is prolonged relative to the rapid blood clearance (inferred from the rapid renal cortical clearance phase).

In Vitro T1 Measurements

In vitro measurements were also performed on the organs imaged in the foregoing in vivo imaging experiment, with results as shown in Table 4.

The T1 changes of organs freshly excised at 40 minutes postcontrast (i.v. injection) from the animals imaged above, indicate significant decreases in the T1's of kidneys for the contrast-injected "A" and "C" animals (relative to the uninjected "B" animal). However, they show no significant decreases in the T1's of livers for the injected versus uninjected animals.

These results confirm the in vivo imaging results and establish that the major route of clearance is renal. They also confirm that there is no significant acute clearance by normal liver.

Similarities and Differences between Agents
Similarities of $Cr_4S$-Heparin and Gd-DTPA-dextran 1. Increased chemical potency (increased proton T1 relaxivity) due to slower rotational correlation time of polymeric versus small molecular contrast agents
2. Restricted initial biodistribution of polymeric contrast agents in vivo (in ca. 10% of body water versus 35% for freely ECF-exchanging, small molecular agents)
   a. increased in vivo potency
   b. potentially decreased in vivo toxicity
3. Advantage of being strong T1-relaxation agents in combination with the newer, more heavily T1-weighted MRI pulse sequences
4. Improved imaging of tumors in body and brain sites, due to improved selectivity of tumor uptake
   a. avoidance of acute uptake by normal liver (unlike standard, small contrast agents)
5. Improved detection of small tumor masses (due to increased contrast gradient at tumor margins)
6. Prolonged enhancement of tumors prior to contrast fading
   a. patient premedication outside of imaging room
   b. acquisition of multiple, sequential images with different pulse sequences prior to contrast fading
   c. imaging of multiple body regions after a single dose
7. Essentially complete aqueous solubility
8. Rapid clearance by the renal route
9. Isosmotic at typical injection concentrations and doses
10. Identification and differentiation of functional tumor subregions (viable versus nonviable), due to slower interstitial diffusion of these polymeric agents relative to standard small molecular agents
    a. improved assessment of viable tumor mass
    b. noninvasive method for monitoring acute tumor-treatment effects.

Advantages of $Cr_4S$-Heparin over Gd-DTPA-dextran

1. $Cr_4S$-heparin has a lower molecular weight (ca. 18,000 daltons) than Gd-DTPA-dextran 70 (ca. 46,000 daltons). (This may lead to improved tumor ACCESS of $Cr_4S$-heparin.)
2. Each $Cr_4S$ ion cluster of $Cr_4S$-heparin contains 4 chromium ions oriented so as to produce magnetic coupling and result in a "superparamagnetic" ion complex which is ca. 1.7 times more potent than a single gadolinium ion (due to the resulting 12 unpaired electrons of $Cr_4S$ versus only 7 for gadolinium.)
3. For $Cr_4S$, increased loading of strongly paramagnetic centers per unit length and weight of polymeric carrier (due to increased net paramagnetism in each polyatomic ion-cluster side group relative to each gadolinium-DTPA side group.
4. The heparin carrier has been established histologically (not shown) to be transported inside tumor cells, rather than just into the extracellular space surrounding tumor cells (this may contribute to prolonged contrast enhancement).
5. Possibly more rapid renal clearance of $Cr_4S$-heparin due to smaller size of polymeric carrier.
6. Possibly increased uptake and more prolonged retention of $Cr_4S$-heparin in tumors due to:
   a. selective active uptake of heparin across lesional (tumor) endothelium; and
   b. selective binding of heparin carrier to tissue matrix components of lesional (tumor) sites, including: fibronectin split products, laminin, collagen fragments, endogenous heparin sulfates and other matrix substances exposed in disease.

NOTE: Heparin which is fully complexed to $Cr_4S$ does not produce significant in vivo anticoagulation (as assessed by the glass-induced clotting time of whole murine blood after intravenous administration of ca. 3 times the effective imaging dose).

TABLE 2

| Absolute Intensities* of Murine Breast Tumor and Vertebral Muscle in MR Images (in vivo) | | |
|---|---|---|
| Group | Intensity of Tumor* (Mean ± 1 SD) | Intensity of Muscle* (Mean ± 1 SD) |
| 1. Precontrast | 4367 ± 553 | 2896 ± 589 |
| 2. Postcontrast 10 minutes | 5723 ± 674 | 2885 ± 631 |
| 3. Postcontrast 30 minutes | 5648 ± 801 | 3003 ± 436 |

*In arbitrary units, based on 20 to 80 image pixels

TABLE 3

| Relative Intensity of Murine Breast Tumor in MR Images (in vivo)* | | |
|---|---|---|
| Group | Intensity of Tumor/Muscle | Increment (%) |
| 1. Precontrast | 1.51 | — |
| 2. Postcontrast 10 minutes | 1.98 | 31 |
| 3. Postcontrast 30 minutes | 1.88 | 25 |

*Data are derived from Table 2 and are based on means of 20 to 80 image pixels

TABLE 4

| T1 Relaxation Times of Freshly Excised Organs 40 Minutes after Injection of Access MRI Contrast Agent | | | |
|---|---|---|---|
| Animal | Organ | T1 (msec)* | % of Control |
| A) Control. | Kidney | 268.5 | 73.2 |

TABLE 4-continued

T1 Relaxation Times of Freshly Excised Organs
40 Minutes after Injection of Access MRI Contrast Agent

| Animal | Organ | T1 (msec)* | % of Control |
|---|---|---|---|
| Injected | Liver | 336.0 | 95.3 |
| B) Control, | Kidney | 367 | Control |
| Uninjected | Liver | 352.5 | Control |
| C) Tumor, | Kidney | 269 | 73.3 |
| Injected | Liver | 343 | 97.3 |
| | Tumor | 553 | — |

*Data are means of 3 to 5 individual measurements

Further Modifications and Variations

It will be recognized by those skilled in the art that the innovative concepts disclosed in the present application can be applied in a wide variety of contexts. Moreover, the preferred implementation can be modified in a tremendous variety of ways. Accordingly, it should be understood that the modifications and variations suggested above are merely illustrative. These examples may help to show some of the scope of the inventive concepts, but these examples do not nearly exhaust the full scope of variations in the disclosed novel concepts.

For example, although the presently preferred embodiment is primarily directed to imaging, the selective transport advantages provided could also be used to enhance the performance of NMR spectroscopy of the human body if desired.

For another example, it is alternatively possible to combine a carrier group with a small therapeutic complex. Combinations of boron (or a boroleptic group which provides a site for boron), or of cis-platinum (more precisely, cis-dichlorodiamine platinum), with a carrier group like those described above may be advantageous. The active agent may be selected to provide chemotherapeutic impact, or to provide sensitization or augmentation for radiation treatment.

For one example, although the disclosed innovations are particularly advantageous in selective transport to tumor sites, they can also be adapted for use with a wide variety of other types of disease or pathology, to selectively address sites where "vascular-permeability-increased" tissue exists. For example, the disclosed innovations can be adapted for use in treatment or imaging (or fine-scale diagnosis) of arthritis, diabetic angiopathy, retinitis, transplantation rejection, or other inflammatory conditions.

Similarly, the disclosed innovative ideas can also be adapted for selectively imaging sclerotic tissue, and thus may be useful in dealing with conditions such as arteriosclerosis or multiple sclerosis.

For yet another example, the disclosed innovative ideas can also be used to monitor rates of drug arrival, release, or backdiffusion.

In a further alternative, synthetic polymers other than CARBETIMER ™ could be used. CARBETIMER ™ is a polyaldehyde/polyamine synthetic polymer, which provides useful transport characteristics as a carrier. Many other such synthetic polymers have been proposed, and could be used, if desired, as the polymer in the carrier.

It should also be noted that the carrier can be used either as a polymer or as a microsphere (or other supermolecular aggregation). Polymers are most preferably given a molecular weight in the range of 15,000 to 40,000 Daltons, as described above; but larger polymer sizes may be advantageous for some applications. In particular, where the toxicity is very low (as with chromium), it may be advantageous to use a polymer whose molecular weight is above the renal clearance limit. In such cases, the resulting clearance time will permit the composition to be used as a "blood pool," where a low blood concentration is available over a long period of time to diffuse into a target site. (This may be particularly useful for therapeutic applications.)

Microspheres are even larger than the largest preferred polymer sizes. For example, a polymer of 200,000 Daltons molecular weight will have a typical maximum dimension of less than 12 nm, whereas a microsphere will have a diameter of 100 nm or more. The present invention may optionally be used with microspheres as large as 250 microns. (The larger microsphere sizes are primarily useful for embolization imaging of lung and tumor, and for imaging body cavities, such as lung, bladder, bowel, or central nervous system cavities.) Microspheres may include a surface coating which provides available reactive groups, such as hydroxyl, carbonyl, aldehyde, carboxylate, sulfate, phosphate and amine groups (singly or in combination), for binding to the complex being transported, whereas these reactive groups need not be present in the matrix of the microsphere. However, it should be noted that the polymers of the microsphere matrix should preferably be completely watersoluble, to facilitate clearance from the body.

It should also be noted that a composition of microspheres, with a diameter between about 0.1 micrometer and about 4.0 micrometers, and a polyatomic metal atom cluster which consists essentially of $(Cr_4S(O_2CCH_3)_8(H_2O)_4)^{+2}$ bound to diethylenetriaminepentaacetate-dextran, diethylenetriamine pentaacetate-hydroxyethyl starch, heparin, dextran sulfate or pentosan polysulfate, is believed to be particularly advantageous for liver imaging.

A further point which should be noted is that carriers (such as dextran) have been ionically coupled to an active agent, to produce drug salts; but it has not been conventional to chelate an active agent to a carrier, as is disclosed in some of the innovative examples above. As the examples above show, this further innovative teaching is believed to provide significant advantages.

For superparamagnetic polyatomic structures, it should be noted that heteropolyatomic structures can be used to reduce the need for binding ligands. For example, it is known that vanadium, cobalt, or tungsten can be used as binding atoms to stabilize the relative positions of chromium atoms.

For another modification of the superparamagnetic polyatomic structures, it is expected that the central coordinating atom (which is sulfur in the $Cr_4S(O_2CCH_3)_8(H_2O)_4^{+2}$ example) could alternatively be tungsten, or even vanadium, molybdenum, cobalt, or other species.

In a further alternative, it has been found that transport of glycerol by a polymeric carrier actually increases the permeability of the vascular walls in the tumorous region. Thus, optionally, this effect can be used to further increase the selectivity of delivery of the desired agent.

Moreover, the varying requirements of various applications may imply a rebalancing of the various factors enumerated. For example, where it is desired to transport a metal ion which is very non-toxic, loose binding to the polymeric carrier may be perfectly acceptable. Conversely, in some cases covalent bonding may be particularly advantageous. Paired-ion embodiments may be advantageous for improved renal excretion. Polymers less than about 45K Daltons are particularly advantageous for rapid renal excretion. (Of course, in assessing the size of a polymer composition, it must be recognized that there will normally be a distribution of sizes actually present. The references to molecular weight of polymers herein generally refer to the molecular number weight, or $M_N$, i.e. the peak of this distribution.)

The following further clarifications are included to facilitate thorough understanding and interpretation of the disclosed teachings.

1. The preferred upper limit of about twelve nanometers, for either the sizes of the carriers or the overall sizes of the carrier-metal atom agents described above, relates to experimental observations that carriers (agents) which are smaller than this approximate size are most readily and rapidly transported across endothelial (or epithelial) barriers to which a subset of the present carriers will bind as a result of their complementarity to endothelial (epithelial) determinants. Such transport (and resulting tissue access) may occur by: a) induced (active) rapid transport across physically intact (nonporous) endothelium (or epithelium); b) passive extravasation through native or induced pores (usually in sites of disease or physically compromised endothelium (or epithelium)); or c) both "a" and "b" in varying ratios, depending on the physiopathologic state of the target tissues (organs).

One of the preferred molecular weight ranges of 15,000–45,000 Daltons for carriers (or carrier-metal atom agents) is based on similar considerations, and also on the experimental observations that, following intravenous administration (or other routes leading to efficient intravenous uptake and circulation): a) molecules larger than about 15,000 Daltons remain predominantly within the vascular compartment except in regions of altered vascular endothelium—chemical or physical (porosity) changes—and, hence, accumulate selectively in extravascular tissue sites based on disease-induced or organ-dependent endothelial (or epithelial) binding, transport and filtration; and b) molecules smaller than about 45,000 Daltons are cleared efficiently by the renal route. The more restricted, preferred molecular weight range for carriers of about 15,000–26,000 Daltons is based on: a) the observation that pharmaceutical heparins purified from natural sources tend to fall into this general molecular weight range; and b) experiments which indicate that carriers (or complete agents) in this lower molecular weight range may undergo the very most rapid transport out of the vascular (or epithelial) compartment into underlying (potentially otherwise sequestered) tissue sites and, hence, may accumulate most efficiently in the selected tissue target sites described above. (This does not exclude, however, that the slightly larger molecular species of 26,000–45,000 Daltons—or even larger ones—could be superior for selective localization under appropriate or specialized conditions.)

In an alternative class of embodiments, lower molecular weights (as low as 1,000 Daltons) may alternatively be used. In this class of embodiments, the composition would typically be designed to bind to circulating plasma substances, and thereby reformulate itself in the body as a functionally polymeric compound (adduct) greater than 15,000 Daltons. (Other uses of these low-MW versions may alternatively be indicated.)

2. In considering the polyatomic metal-atom complexes described above, the term "bridging ligands" extends to include both atoms and molecules and both organic and inorganic molecules. Thus, in heteropolyatomic metal-atom complexes, secondary metal atoms (paramagnetic or non-paramagnetic ones), as well as acetate, glycinate or other molecules, may serve as all or some of the bridging ligands for the primary (paramagnetic or therapeutic) metal atoms.

3. The weight ratios and molar ratios of (polyatomic) metal-atom complex-to-carrier substance are based on the following. Present examples teach that greater than about 35% (w/w) metal-atom complex-to-carrier can be achieved for $Cr_4S$-heparin, and even higher weight ratios are referenced as possible to achieve for hydrophilic microsphere-entrapped substrates. Hence an upper limit molar ratio of about 1:2 (or about 50% w/w) is referenced here. A lower limit molar ratio of about 1:25 (or about 5% w/w) derives from: a) present examples; b) the applicant's previous patent applications (referenced above); and, importantly, c) the requirement of at least about a 5% (w/w) content of polyatomic metal-atom complex in order to achieve sufficient superparamagnetic (strongly paramagnetic) tissue proton effects for tissue visualization of intravenously injected agent, and simultaneous avoidance of unacceptably large, acute plasma expansion due to osmotic effects of the macromolecular carriers. (Those skilled in the art will recognize that molar ratios and weight ratios are not directly equivalent, but vary with the molecular weights of the individual metal-atom complexes and polymeric carriers.)

4. For present purposes, the definition of "multiply paired-ion strong association" is as follows: "Two or more ionic charges each, of a positive and negative sign, located in close molecular proximity on the binding and bound groups, together with sufficient ionization of these charged groups at physiologic pH, to confer a chemical association which is sufficiently strong to give stable ion pairing in the presence of plasma or body fluids during localization and clearance of said metal-atom-carrier complexes (as elucidated in the preceding examples).

5. For the various metal atoms described above, it is emphasized here that numerous different metals may serve as either or both diagnostic or therapeutic agents (including $^{(195)}$platinum, gadolinium, boron, gold and others). Hence, they are included together in the present application, and are considered all to be variations of a single, unified approach to preparing compositions of matter involving (polyatomic or other) metal-atom-complex carriers. In terms of various pharmaceutical applications, platinum is used as a chemotherapeutic as well as potentially a paramagnetic agent for MRI diagnosis; and boron and boroleptics (boron complexes) can be used either as therapeutic radiation enhancers or as diagnostic agents, as can gold salts. Gold salts and metal-atom coordinates (including, among others, the therapeutic antiinflammatory/antiarthritic agent Auraofin TM) can be administered for therapeutic purposes by formulating these salts (coordinates) as the metal-atom complexes described above. Hence, the single nature and structural category of these metal-atom-carrier compositions is apparent and supported in a fashion independent of their potentially multiple diagnostic and therapeutic pharmaceutical indications.

As will be recognized by those skilled in the art, the innovative concepts described in the present application can be modified and varied over a tremendous range of applications, and accordingly their scope is not limited except by the allowed claims.

What is claimed is:

1. A composition of matter comprising
   a superparamagnetic polyatomic metal atom complex, containing plural paramagnetic metal atoms which are intramolecularly ferromagnetically coupled, and including bridging ligands bound to said paramagnetic metal atoms, said polyatomic metal complex consisting essentially of four Cr(III) atoms which are bound to a central tetrahedral sulfur atom and are octahedrally coordinated by bridging ligands,
   said polyatomic complex being bound to or associated with:
   a biocompatible and at least substantially water-soluble anionic carbohydrate, oligosaccharide, polysaccharide, or glycosaminoglycan carrier;
   said carrier having repeating hydrophilic units which contain covalently bound available reactive groups selected from the group consisting of hydroxyl, carbonyl, aldehyde, carboxylate, sulfate, phosphate and amine groups,
   wherein said polyatomic metal atom complex is in a molar ratio to individual repeating units of said carrier of between about 1:2 and about 1:25.

2. The composition of claim 1 defined further, wherein said carrier is complementary to determinants of vertebrate endothelia or epithelia.

3. The composition of claim 1, defined further as an in vivo diagnostic agent for enhancing internal images or shifting internal spectra arising from induced magnetic resonance signals.

4. The composition of claim 1, wherein said carrier has a molecular weight between about 1,000 and about 200,000 Daltons.

5. The composition of claim 1, wherein said carrier has a molecular weight between about 15,000 and about 45,000 Daltons.

6. The composition of claim 1, wherein said polyatomic metal atom complex is bound to said carrier non-covalently by a strong ionic, paired-ion or charge interaction.

7. The composition of claim 6, wherein said strong interaction is by chemical coordination or chelation binding of said polyatomic metal atom complex to one or more of said reactive groups of said polymer, each site of said coordination or chelation binding, on said carrier, having a coordination number or ionic charge number of between 2 and 10 inclusive.

8. The composition of claim 1, wherein said polyatomic metal atom complex is covalently conjugated to said carrier.

9. The composition of claim 8, wherein said covalent conjugation of said polyatomic metal atom complex to said carrier is by a metal-oxide bond or a direct metal bond to said carrier.

10. The composition of claim 1, wherein said carrier has a molecular size of less than about twelve nanometers, and said carrier contains less than about 5% (w/w) cross-linked or microaggregated species.

11. The composition of claim 1 wherein said water-soluble carrier is dextran, dextran sulfate, carboxymethyl dextran, dicarboxyethyl dextran, succinylated dextran, diethylenetriaminepentaacetate-dextran, dicarboxyethylhydroxyethyl starch, carboxymethylhydroxyethyl starch, succinylated hydroxyethyl starch, diethylenetriamine pentaacetate-starch, heparin, heparan sulfate, dermatan sulfate, pentosan polysulfate, dicarboxyethyl heparin, a heparin fragment, succinylated heparin, or diethylenetriaminepentaacetate-heparin.

12. The composition of claim 1, wherein said bridging ligands are acetate groups and said polyatomic metal atom complex consists essentially of $Cr_4S(O_2CCH_3)_8(H_2O)_4^{+2}$.

13. The composition of claim 1, wherein said polyatomic metal atom complex has the formula $(Cr_4SR_nC_m)$, where R is a bridging ligand of formate, formaldehyde, glutaraldehyde, acetate, glycinate, succinate, acetylacetonate, malonate, propionate, glutarate, hydroxamate, oxalate, 2-bromoacetate, 2-sulfoethanoate, thiolacetate or thioglycolate; n is the number of R groups per metal atom complex, numbering between 4 and 12; C is a stabilizing counterion selected from the group consisting of water, halide, sulfate, nitrate, carboxylate, and phosphate; and m is between 1 and 2n.

14. The composition of claim 13 defined further, wherein said bridging is a combination of acetate and glycinate groups at a molar ratio of between about 1 and about 3 glycinates per polyatomic complex and amino groups of said glycinate assist in binding said polyatomic complex to said carrier.

15. The composition of claim 1, wherein said carrier consists essentially of heparin, or a heparin fragment.

16. The composition of claim 1, wherein said carrier has a molecular weight of between 15,000 and 26,000 Daltons.

17. The composition of claim 1, wherein said polyatomic metal atom complex is $Cr_4S(O_2CCH_3)_8$, and said carrier consists essentially of dextran, carboxymethyl dextran, dicarboxyethyldextran, succinylated dextran, diethylenetriamine pentaacetate-dextran or dextran sulfate.

18. The composition of claim 1, wherein said polyatomic metal atom complex is $Cr_4S(O_2CCH_3)_8$, and said carrier consists essentially of hydroxyethyl starch, carboxymethyl hydroxyethyl starch, dicarboxyethyl hydroxyethyl starch, succinylated hydroxyethyl starch or diethylenetriamine pentaacetate-starch.

19. The composition of claim 2, wherein said polyatomic metal atom complex is $Cr_4S(O_2CCH_3)_8$, and said carrier consists essentially of heparin, dicarboxyethyl heparin, carboxymethyl heparin, succinylated heparin or diethylenetriamine pentaacetate-heparin.

20. The composition of claim 1, wherein said polyatomic metal atom complex and said carrier are formulated as microspheres with a diameter between 0.1 micrometers and about 250 micrometers.

21. The composition of claim 20, wherein said microspheres have a diameter between about 0.1 micrometer and about 4.0 micrometers, and said polyatomic metal atom cluster consists essentially of $(Cr_4S(O_2CCH_3)_8(H_2O)_4)^{+2}$ bound to diethylenetriamine pentaacetate-dextran, diethylenetriamine pentaacetate-hydroxyethyl starch, heparin, dextran sulfate or pentosan polysulfate.

22. A method for magnetic resonance imaging, comprising the steps of:
   identifying a living vertebrate animal to be imaged;
   introducing into the blood stream or body cavity of said animal a diagnostically effective amount of a diagnostic imaging agent comprising an at least substantially water-soluble anionic carrier with a molecular weight of greater than about 1,000 Daltons, and also includes plural superparamagnetic polyatomic metal atom complexes associated with said carrier, each of polyatomic metal atom complexes including plural paramagnetic metal atoms which are intramolecularly ferromagnetically coupled metal, said polyatomic metal complexes consisting essentially of four Cr(III) atoms which are bound to a central tetrahedral sulfur atom and are octahedrally coordinated by bridging ligands;

applying to said animal a strong magnetic field which includes a gradient; and applying to at least a portion of said animal an electromagnetic perturbation field at a radio frequency corresponding to a resonant frequency of a predetermined atomic nucleus at a magnetic field strength which falls within a range of field strengths applied to said animal by said strong magnetic field, and measuring radio frequency emissions to define a spatial map of magnetic resonance characteristics within tissues of said animal.

23. The method of claim 22, wherein said carrier molecule has a molecular weight of about 15,000 to 45,000 Daltons.

24. The method of claim 22, wherein said carrier consists essentially of heparin or a heparin fragment.

25. The method of claim 22, wherein said carrier consists essentially of heparin, or a heparin fragment, and the size of said polymeric compound is less than about twelve nanometers, and said superparamagnetic polyatomic complex consists essentially of $Cr_4S(O_2CCH_3)_8(H_2O)_4{}^{+2}$.

26. The method of claim 22, wherein said superparamagnetic polyatomic complex consists essentially of $Cr_4S(O_2CCH_3)_8(H_2O)_4{}^{+2}$.

27. A composition of matter comprising a superparamagnetic polyatomic metal atom complex, containing plural paramagnetic metal atoms which are intramolecularly ferromagnetically coupled, and including bridging ligands bound to said paramagnetic metal atoms, said polyatomic metal complex consisting essentially of four Cr(III) atoms which are bound to a central tetrahedral sulfur atom and are octahedrally coordinated by bridging ligands, said polyatomic complex being bound to or associated with:

a biocompatible and at least substantially water-soluble anionic carbohydrate, oligosaccharide, polysaccharide, or glycosaminoglycan carrier;

said carrier having repeating hydrophilic units which contain covalently bound available reactive groups selected from the group consisting of hydroxyl, carbonyl, aldehyde, carboxylate, sulfate, phosphate and amine groups, wherein said carrier is complementary to determinants of vertebrate endothelia or epithelia, wherein said polyatomic metal atom complex is in a molar ratio to individual repeating units of said carrier of between about 1:2 and about 1:25.

28. A composition of matter comprising a superparamagnetic polyatomic metal atom complex, containing plural paramagnetic metal atoms which are intramolecularly ferromagnetically coupled, and including bridging ligands bound to said paramagnetic metal atoms, said polyatomic metal complex consisting essentially of four Cr(III) atoms which are bound to a central tetrahedral sulfur atom and are octahedrally coordinated by bridging ligands, said polyatomic complex being bound to or associated with:

a biocompatible and at least substantially water-soluble carbohydrate, oligosaccharide, polysaccharide, or glycosaminoglycan carrier;

said carrier having repeating hydrophilic units which contain covalently bound available reactive carboxylate or sulfate groups, wherein said polyatomic metal atom complex is in a molar ratio to individual repeating units of said carrier of between about 1:2 and about 1:25.

29. A composition of matter comprising a superparamagnetic polyatomic metal atom complex, containing plural paramagnetic metal atoms which are intramolecularly ferromagnetically coupled, and including bridging ligands bound to said paramagnetic metal atoms, said polyatomic metal complex consisting essentially of four Cr(III) atoms which are bound to a central tetrahedral sulfur atom and are octahedrally coordinated by bridging ligands, said polyatomic complex being bound to or associated with:

a biocompatible and at least substantially water-soluble carbohydrate, oligosaccharide, polysaccharide, or glycosaminoglycan carrier;

said carrier having repeating hydrophilic units which contain covalently bound available reactive groups selected from the group consisting of carboxylate and sulfate, wherein said carrier is complementary to determinants of vertebrate endothelia or epithelia, wherein said polyatomic metal atom complex is in a molar ratio to individual repeating units of said carrier of between about 1:2 and about 1:25.

* * * * *